US009600922B2

(12) United States Patent
Tsukagoshi et al.

(10) Patent No.: US 9,600,922 B2
(45) Date of Patent: Mar. 21, 2017

(54) SYSTEM, APPARATUS, AND METHOD FOR IMAGE PROCESSING AND MEDICAL IMAGE DIAGNOSIS APPARATUS

(71) Applicant: Toshiba Medical Systems Corporation, Otawara-shi (JP)

(72) Inventors: Shinsuke Tsukagoshi, Nasushiobara (JP); Takashi Tsutsumi, Utsunomiya (JP); Yasuko Fujisawa, Nasushiobara (JP); Manabu Teshigawara, Otawara (JP); Akira Adachi, Otawara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 364 days.

(21) Appl. No.: 14/158,123

(22) Filed: Jan. 17, 2014

(65) Prior Publication Data

US 2014/0132597 A1 May 15, 2014

Related U.S. Application Data

(63) Continuation of application No. PCT/JP2012/068482, filed on Jul. 20, 2012.

(30) Foreign Application Priority Data

Jul. 20, 2011 (JP) .................................. 2011-159205

(51) Int. Cl.
*G06T 7/00* (2006.01)
*A61B 6/03* (2006.01)
(Continued)

(52) U.S. Cl.
CPC .............. *G06T 15/00* (2013.01); *A61B 8/483* (2013.01); *G06T 7/0028* (2013.01);
(Continued)

(58) Field of Classification Search
CPC ................. G06T 7/0024; G06T 7/0012; G06T 2207/10081; A61B 6/032
See application file for complete search history.

(56) References Cited

U.S. PATENT DOCUMENTS

2001/0007919 A1* 7/2001 Shahidi .................... A61B 5/06
600/427
2005/0083246 A1 4/2005 Saishu et al.
(Continued)

FOREIGN PATENT DOCUMENTS

JP 2005-086414 A 3/2005
JP 2005-199057 A 7/2005
(Continued)

OTHER PUBLICATIONS

International Search Report issued on Aug. 28, 2012 for PCT/JP2012/068482 filed on Jul. 20, 2012 with English Translation.
(Continued)

*Primary Examiner* — Matthew Salvucci
(74) *Attorney, Agent, or Firm* — Oblon, McClelland, Maier & Neustadt, L.L.P.

(57) ABSTRACT

In an image processing apparatus, an extracting unit extracts mutually the same region of interest from each of a plurality of pieces of three-dimensional image data corresponding to mutually-different time phases. Further, a position determining unit determines, on the basis of feature points included in the pieces of three-dimensional image data, a position used for superimposing together the regions of interest extracted by the extracting unit from the pieces of three-dimensional image data, in substantially the same position of a subject. After that, a display controlling unit changes a display format of each of the regions of interest extracted by the extracting unit from the pieces of three-dimensional image data so as to be mutually different and causes a
(Continued)

superimposed image to be displayed by superimposing the regions of interest together in the position determined by the position determining unit.

6 Claims, 14 Drawing Sheets

(51) Int. Cl.
  *G06T 15/00* (2011.01)
  *G06T 15/08* (2011.01)
  *G06T 19/20* (2011.01)
  *A61B 8/08* (2006.01)
  *A61B 5/055* (2006.01)
  *A61B 6/00* (2006.01)
  *A61B 8/00* (2006.01)

(52) U.S. Cl.
  CPC .......... *G06T 7/0081* (2013.01); *G06T 7/0097* (2013.01); *G06T 15/08* (2013.01); *G06T 19/20* (2013.01); *A61B 5/055* (2013.01); *A61B 6/466* (2013.01); *A61B 8/466* (2013.01); *A61B 2576/023* (2013.01); *G06T 7/0012* (2013.01); *G06T 7/0024* (2013.01); *G06T 2207/10081* (2013.01); *G06T 2207/30096* (2013.01); *G06T 2210/41* (2013.01); *G06T 2219/2004* (2013.01)

(56) References Cited

U.S. PATENT DOCUMENTS

| | | |
|---|---|---|
| 2005/0135707 A1 | 6/2005 | Turek et al. |
| 2005/0244036 A1* | 11/2005 | Rusinek ................ G06T 7/0012 382/120 |
| 2007/0092067 A1 | 4/2007 | Fujisawa |
| 2010/0195883 A1* | 8/2010 | Patriarche ............ G06K 9/3233 382/131 |
| 2011/0043615 A1 | 2/2011 | Saishu et al. |
| 2011/0137156 A1* | 6/2011 | Razzaque .......... A61B 19/5244 600/424 |
| 2012/0139911 A1 | 6/2012 | Saishu et al. |

FOREIGN PATENT DOCUMENTS

| | | |
|---|---|---|
| JP | 2007-117384 A | 5/2007 |
| JP | 2007-136164 A | 6/2007 |
| JP | 2008-119071 A | 5/2008 |

OTHER PUBLICATIONS

International Written Opinion mailed on Aug. 28, 2012 for PCT/JP2012/068482 filed on Jul. 20, 2012.

* cited by examiner

FIG.8
(A)
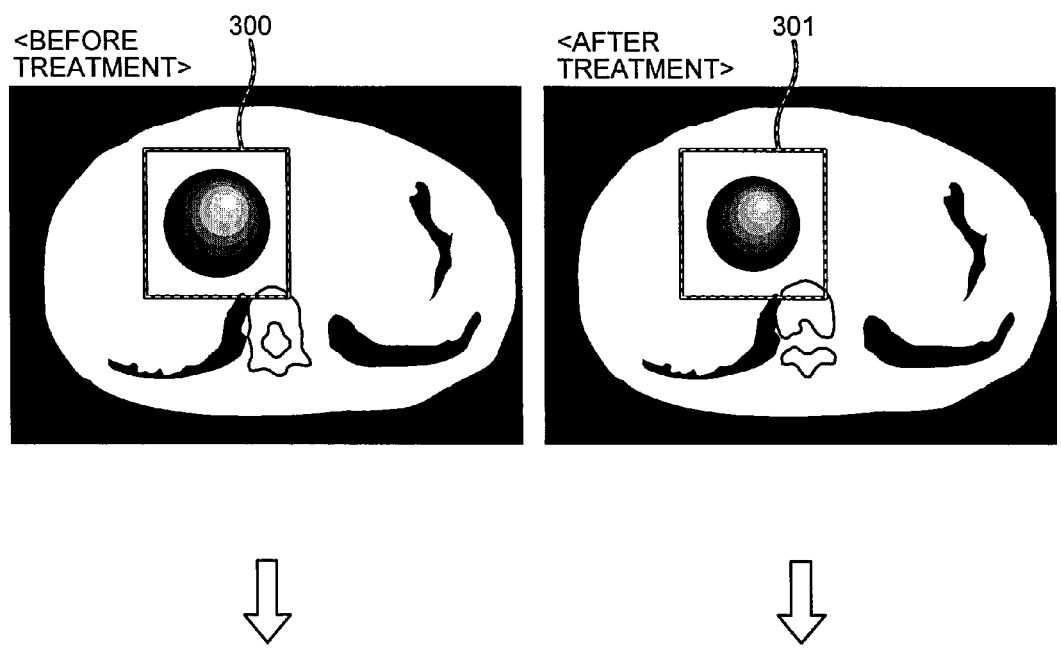
(B)
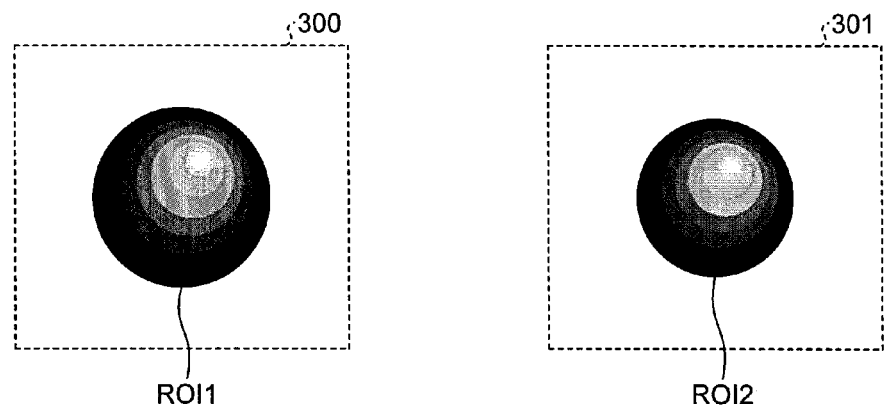

FIG.10
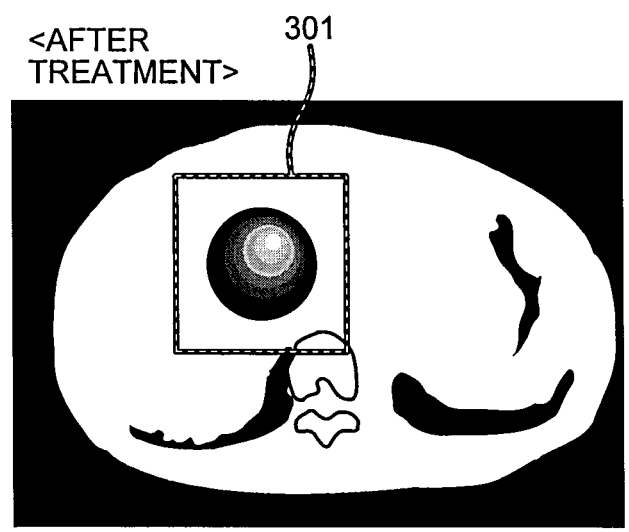
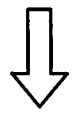
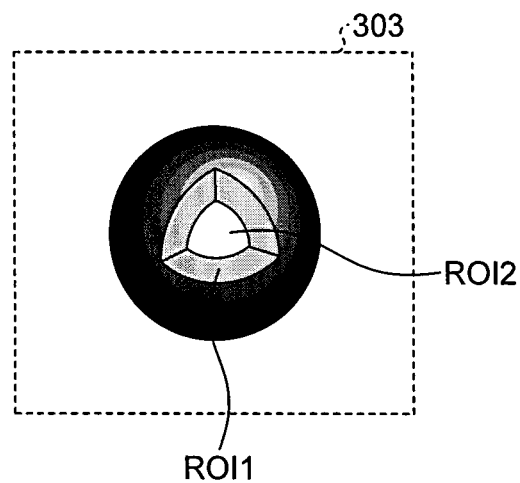

FIG.13
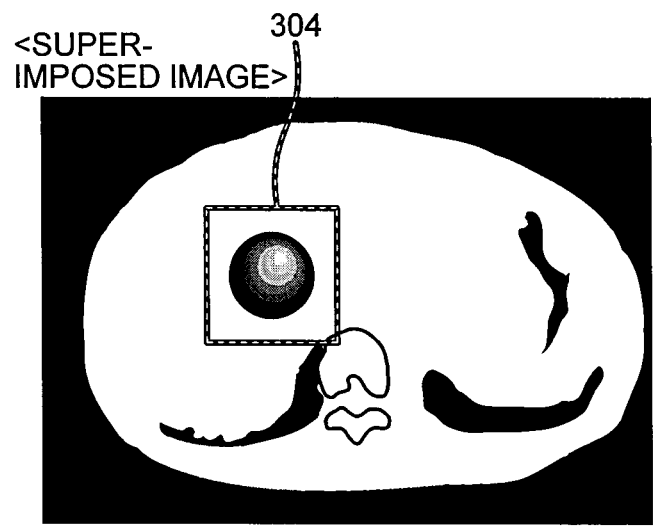
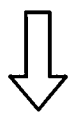
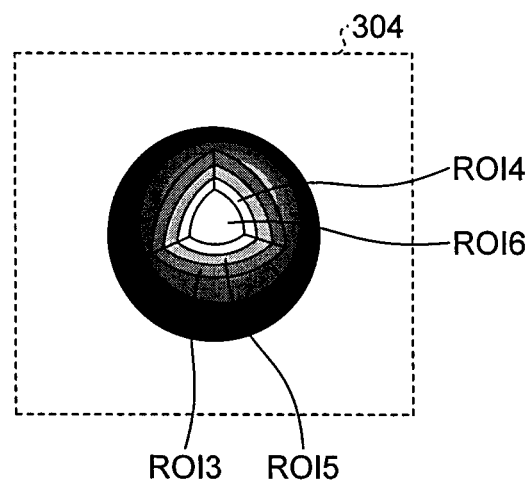

FIG.14
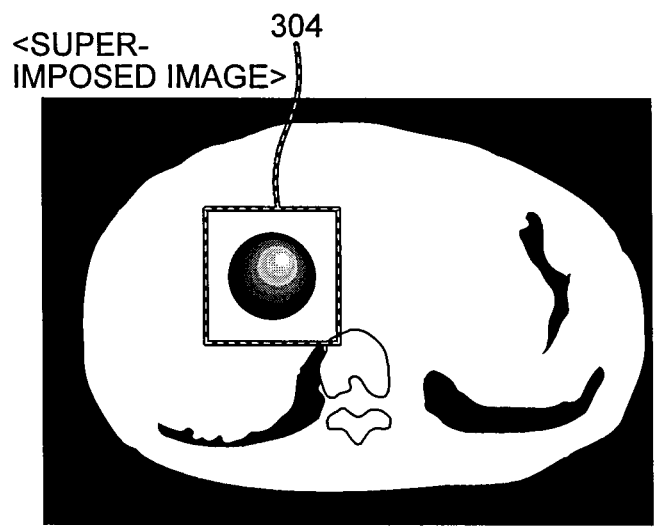
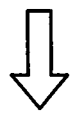
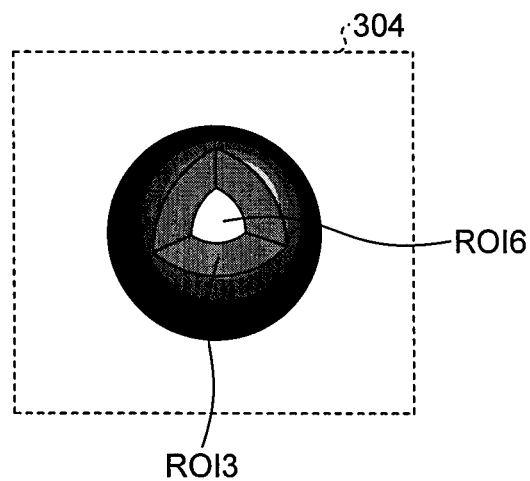

FIG.15
<CT IMAGE>
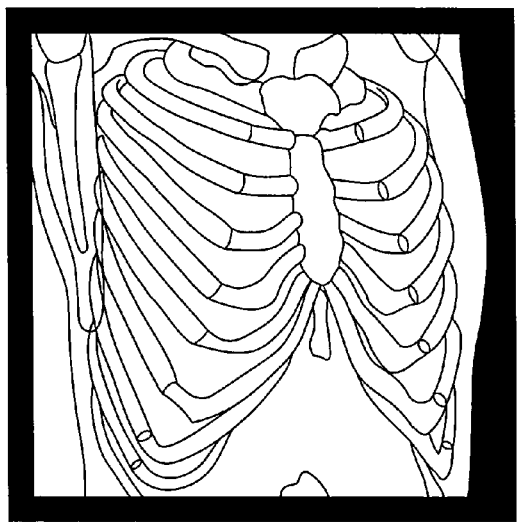
<PET IMAGE>
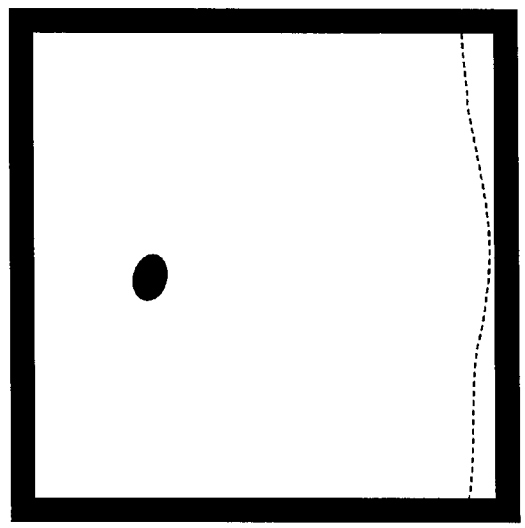
<FUSED IMAGE>
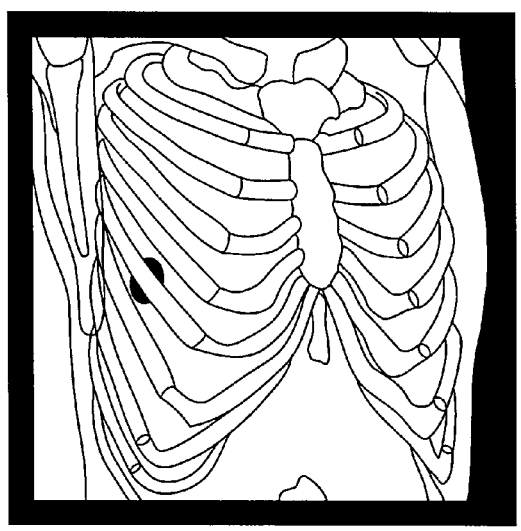

SYSTEM, APPARATUS, AND METHOD FOR IMAGE PROCESSING AND MEDICAL IMAGE DIAGNOSIS APPARATUS

CROSS-REFERENCE TO RELATED APPLICATIONS

This application is a continuation of International Application No. PCT/JP2012/068482, filed on Jul. 20, 2012 which claims the benefit of priority of the prior Japanese Patent Application No. 2011-159205, filed on Jul. 20, 2011, the entire contents of which are incorporated herein by reference.

FIELD

Embodiments described herein relate generally to a system, an apparatus, and a method for image processing and a medical image diagnosis apparatus.

BACKGROUND

Conventionally, monitors capable of providing, with the use of an exclusive-use device such as stereoscopic glasses, a stereoscopic view of two-eye disparity images taken from two viewpoints have been in practical use. Further, in recent years, monitors capable of providing, with the use of a light beam controller such as a lenticular lens, a glass-free stereoscopic view of multiple-eye disparity images (e.g., nine-eye disparity images) taken from a plurality of viewpoints have also been in practical use. The two-eye disparity images and the nine-eye disparity images displayed on the monitors capable of providing a stereoscopic view may be generated, in some situations, by estimating depth information of an image taken from one viewpoint and performing image processing while using the estimated information.

Incidentally, as for medical image diagnosis apparatuses such as X-ray Computed Tomography (CT) apparatuses, Magnetic Resonance Imaging (MRI) apparatuses, and ultrasound diagnosis apparatuses, such apparatuses have been in practical use that are capable of generating three-dimensional medical image data (hereinafter, "volume data"). Conventionally, the volume data generated by such a medical image diagnosis apparatus is processed into a two-dimensional image as a result of various types of image processing and is displayed two-dimensionally on a general-purpose monitor. For example, the volume data generated by the medical image diagnosis apparatus is processed into a two-dimensional image that reflects three-dimensional information as a result of a volume rendering process and is displayed two-dimensionally on a general-purpose monitor. According to the conventional technique, however, when a plurality of images corresponding to mutually-different time phases is superimposed together, there are some situations where it is difficult to view the images.

BRIEF DESCRIPTION OF THE DRAWINGS

FIG. 8 contains drawings for explaining an example of a process performed by an extracting unit according to the first embodiment;

FIG. 10 is a drawing for explaining an example of a process performed by a display controlling unit according to the first embodiment;

FIG. 13 is a drawing for explaining a first example of a process performed by a display controlling unit according to the second embodiment;

FIG. 14 is a drawing for explaining a second example of a process performed by the display controlling unit according to the second embodiment; and FIG. 15 is a drawing for explaining an example of a process performed by an extracting unit according to a third embodiment.

DETAILED DESCRIPTION

According to an embodiment, an image processing system includes an extracting unit, a position determining unit and a display controlling unit. The extracting unit configured to extract a mutually-same region of interest from each of a plurality of pieces of three-dimensional image data corresponding to mutually-different time phases. The position determining unit configured to determine, on a basis of feature points included in the pieces of three-dimensional image data, a position used for superimposing together the regions of interest extracted by the extracting unit from the pieces of three-dimensional image data, in a substantially same position of a subject. The display controlling unit configured to change a display format of each of the regions of interest extracted by the extracting unit from the pieces of three-dimensional image data so as to be mutually different and configured to cause a superimposed image to be displayed by superimposing the regions of interest together in the position determined by the position determining unit.

Exemplary embodiments of a system, an apparatus, and a method for image processing and a medical image diagnosis apparatus will be explained in detail, with reference to the accompanying drawings. In the following sections, an image processing system including a workstation that has functions of an image processing apparatus will be explained as an exemplary embodiment. First, some of the terms used in the description of the exemplary embodiments below will be defined. The term "a group of disparity images" refers to a group of images generated by performing a volume rendering process on volume data while shifting the viewpoint position by a predetermined disparity angle at a time. In other words, the "group of disparity images" is made up of a plurality of "disparity images" having mutually-different "viewpoint positions". The term "disparity angle" refers to an angle determined by two viewpoint positions positioned adjacent to each other among viewpoint positions that have been set for generating "a group of disparity images" and a predetermined position in a space (e.g., the center of the space) expressed by the volume data. The term "disparity number" refers to the number of "disparity images" required to realize a stereoscopic view on a stereoscopic display monitor. Further, the term "nine-eye disparity images" used herein refers to "a group of disparity images" made up of nine "disparity images". The term "two-eye disparity images" used herein refers to "a group of disparity images" made up of two "disparity images".

Figure 1:
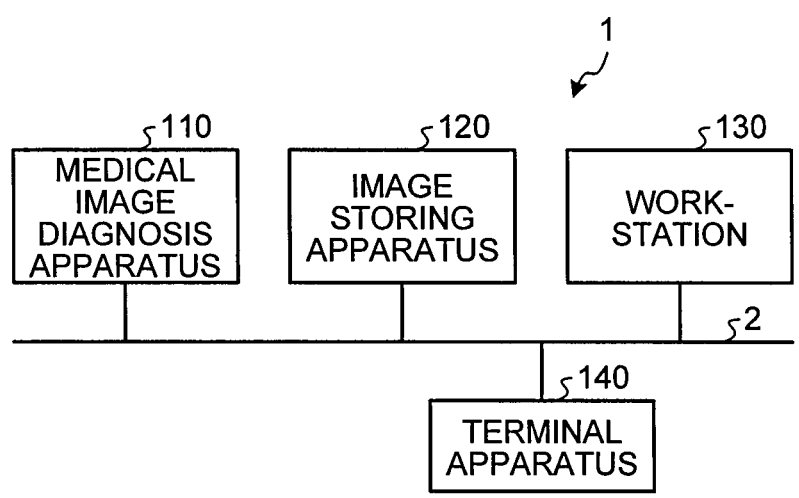
FIG. 1 is a drawing for explaining an exemplary configuration of an image processing system according to a first embodiment.

First, an exemplary configuration of an image processing system according to a first embodiment will be explained. FIG. 1 is a drawing for explaining the exemplary configuration of the image processing system according to the first embodiment.

As shown in FIG. 1, an image processing system 1 according to the first embodiment includes a medical image diagnosis apparatus 110, an image storing apparatus 120, a workstation 130, and a terminal apparatus 140. The apparatuses illustrated in FIG. 1 are able to communicate with one another directly or indirectly via, for example, an intra-hospital Local Area Network (LAN) 2 set up in a hospital. For example, if a Picture Archiving and Communication System (PACS) has been introduced into the image processing system 1, the apparatuses send and receive medical images and the like to and from one another according to the Digital Imaging and Communications in Medicine (DICOM) standard.

The image processing system 1 provides a medical doctor, a laboratory technician, or the like working in the hospital with a medical image capable of providing a stereoscopic view, by generating a group of disparity images from volume data that is three-dimensional medical image data generated by the medical image diagnosis apparatus 110 and displaying the generated group of disparity images on a monitor capable of providing a stereoscopic view. More specifically, according to the first embodiment, the workstation 130 generates the group of disparity images by performing various types of image processing processes on the volume data. Further, the workstation 130 and the terminal apparatus 140 each have a monitor capable of providing a stereoscopic view and are configured to display the group of disparity images generated by the workstation 130 on the monitor. Further, the image storing apparatus 120 stores therein the volume data generated by the medical image diagnosis apparatus 110 and the group of disparity images generated by the workstation 130. In other words, the workstation 130 and the terminal apparatus 140 obtain the volume data and/or the group of disparity images from the image storing apparatus 120 and process or display on the monitor, the obtained volume data and/or the obtained group of disparity images. In the following sections, the apparatuses will be explained one by one.

The medical image diagnosis apparatus 110 may be an X-ray diagnosis apparatus, an X-ray Computed Tomography (CT) apparatus, a Magnetic Resonance Imaging (MRI) apparatus, an ultrasound diagnosis apparatus, a Single Photon Emission Computed Tomography (SPECT) apparatus, a Positron Emission computed Tomography (PET) apparatus, a SPECT-CT apparatus having a SPECT apparatus and an X-ray CT apparatus incorporated therein, a PET-CT apparatus having a PET apparatus and an X-ray CT apparatus incorporated therein, or a group of apparatuses made up of any of these apparatuses. Further, the medical image diagnosis apparatus 110 according to the first embodiment is capable of generating the three-dimensional medical image data (the volume data).

More specifically, the medical image diagnosis apparatus 110 according to the first embodiment generates the volume data by taking images of a subject (hereinafter, "patient"). For example, the medical image diagnosis apparatus 110 acquires data such as projection data or Magnetic Resonance (MR) signals by taking images of the subject and generates the volume data by reconstructing medical image data on a plurality of axial planes along the body-axis direction of the subject from the acquired data. For example, the medical image diagnosis apparatus 110 reconstructs medical image data representing 500 images on axial planes. A group made up of pieces of medical image data representing the 500 images on the axial planes serves as the volume data. Alternatively, the projection data itself or the MR signals themselves of the subject resulting from the image taking process performed by the medical image diagnosis apparatus 110 may serve as the volume data.

Further, the medical image diagnosis apparatus 110 according to the first embodiment sends the generated volume data to the image storing apparatus 120. When sending the volume data to the image storing apparatus 120, the medical image diagnosis apparatus 110 also sends additional information such as a patient ID identifying the patient, a medical examination ID identifying a medical examination, an apparatus ID identifying the medical image diagnosis apparatus 110, a series ID identifying the one image-taking process performed by the medical image diagnosis apparatus 110, and/or the like.

The image storing apparatus 120 is a database configured to store therein medical images. More specifically, the image storing apparatus 120 according to the first embodiment puts the volume data sent thereto from the medical image diagnosis apparatus 110 into a storage unit so as to store the volume data. Also, according to the first embodiment, the workstation 130 generates the group of disparity images from the volume data and sends the generated group of disparity images to the image storing apparatus 120. Thus, the image storing apparatus 120 puts the group of disparity images sent thereto from the workstation 130 into a storage unit so as to store the group of disparity images. By configuring the workstation 130 so as to be able to store therein a large volume of images, the workstation 130 and the image storing apparatus 120 according to the first embodiment illustrated in FIG. 1 may be integrated together. In other words, it is acceptable to configure the first embodiment in such a manner that the volume data or the group of disparity images is stored in the workstation 130 itself.

In the first embodiment, the volume data and the group of disparity images stored in the image storing apparatus 120 are stored while being kept in correspondence with the patient ID, the medical examination ID, the apparatus ID, the series ID, and/or the like. Thus, the workstation 130 and the terminal apparatus 140 are able to obtain a required piece of volume data or a required group of disparity images from the image storing apparatus 120, by conducting a search using a patient ID, a medical examination ID, an apparatus ID, a series ID, and/or the like.

The workstation 130 is an image processing apparatus configured to perform an image processing process on medical images. More specifically, the workstation 130 according to the first embodiment generates the group of disparity images by performing various types of rendering processes on the volume data obtained from the image storing apparatus 120. The "group of disparity images" refers to a plurality of disparity images taken from a plurality of viewpoints. For example, a group of disparity images that is displayed on a monitor capable of providing a glass-free stereoscopic view of nine-eye disparity images is made up of nine disparity images having mutually-different viewpoint positions.

Further, the workstation 130 according to the first embodiment includes, as a display unit, a monitor capable of providing a stereoscopic view (hereinafter, "stereoscopic display monitor"). The workstation 130 generates the group of disparity images and displays the generated group of disparity images on the stereoscopic display monitor. As a result, an operator of the workstation 130 is able to perform an operation to generate a group of disparity images, while viewing the medical images that are capable of providing a stereoscopic view and are being displayed on the stereoscopic display monitor.

Further, the workstation 130 sends the generated group of disparity images to the image storing apparatus 120. When sending the group of disparity images to the image storing apparatus 120, the workstation 130 also sends additional information such as the patient ID, the medical examination ID, the apparatus ID, the series ID, and/or the like. Further, the additional information that is sent when the group of disparity images is sent to the image storing apparatus 120 may include additional information related to the group of disparity images. Examples of the additional information related to the group of disparity images include the number of disparity images (e.g., "9") and the resolution of the disparity images (e.g., "466×350 pixels").

The terminal apparatus 140 is an apparatus used for having the medical images viewed by the medical doctors and the laboratory technicians working in the hospital. For example, the terminal apparatus 140 may be a personal computer (PC), a tablet-style PC, a Personal Digital Assistant (PDA), a portable phone, or the like operated by any of the medical doctors and the laboratory technicians working in the hospital. More specifically, the terminal apparatus 140 according to the first embodiment includes, as a display unit, a stereoscopic display monitor. Further, the terminal apparatus 140 obtains the group of disparity images from the image storing apparatus 120 and displays the obtained group of disparity images on the stereoscopic display monitor. As a result, any of the medical doctors and the laboratory technician serving as a viewer is able to view the medical images capable of providing a stereoscopic view.

Next, the stereoscopic display monitors included in the workstation 130 and the terminal apparatus 140 will be explained. Commonly-used general-purpose monitors that are currently most popularly used are configured to display two-dimensional images in a two-dimensional manner and are not capable of stereoscopically displaying two-dimensional images. If a viewer wishes to have a stereoscopic view on a general-purpose monitor, the apparatus that outputs images to the general-purpose monitor needs to cause two-eye disparity images capable of providing the viewer with a stereoscopic view to be displayed side by side, by using a parallel view method or a cross-eyed view method. Alternatively, the apparatus that outputs images to a general-purpose monitor needs to cause images capable of providing the viewer with a stereoscopic view to be displayed by, for example, using an anaglyphic method that requires glasses having red cellophane attached to the left-eye part thereof and blue cellophane attached to the right-eye part thereof.

As for an example of the stereoscopic display monitor, a monitor is known that is capable of providing a stereoscopic view of two-eye disparity images (may be called "binocular disparity images"), with the use of an exclusive-use device such as stereoscopic glasses.

Figure 2A:
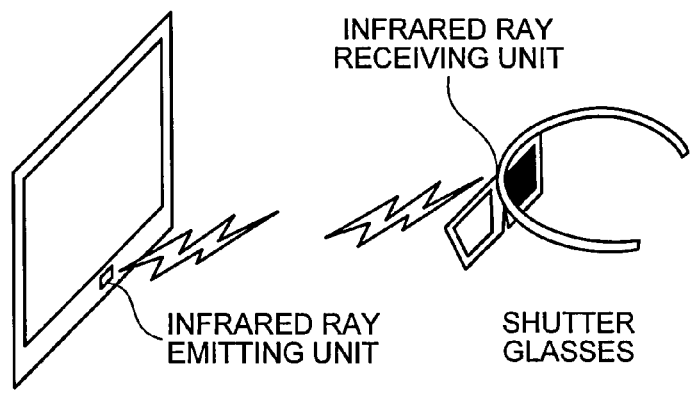
FIG. 2A is a drawing for explaining an example of a stereoscopic display monitor that realizes a stereoscopic display by using two-eye disparity images.
Figure 2B:
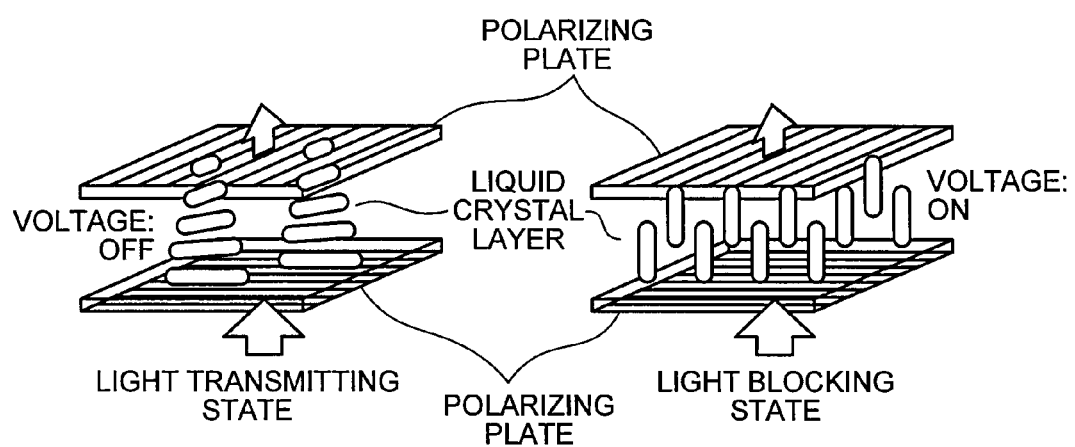
FIG. 2B is another drawing for explaining the example of the stereoscopic display monitor that realizes the stereoscopic display by using the two-eye disparity images.

FIGS. 2A and 2B are drawings for explaining an example of a stereoscopic display monitor that realizes a stereoscopic display by using two-eye disparity images. The example shown in FIGS. 2A and 2B illustrates a stereoscopic display monitor that realizes a stereoscopic display by using a shutter method and uses shutter glasses as the stereoscopic glasses worn by the viewer who looks at the monitor. The stereoscopic display monitor is configured to alternately emit two-eye disparity images from the monitor. For example, the monitor shown in FIG. 2A emits images to be viewed by the left eye (hereinafter, "left-eye images") and images to be viewed by the right eye (hereinafter, "right-eye images") alternately at 120 Hz. In this situation, as shown in FIG. 2A, the monitor is provided with an infrared ray emitting unit, which controls emissions of infrared rays in synchronization with the timing with which the images are switched.

The infrared rays emitted from the infrared ray emitting unit are received by an infrared ray receiving unit of the shutter glasses shown in FIG. 2A. Each of the left and right frames of the shutter glasses has a shutter attached thereto, so that the shutter glasses are able to alternately switch between a light transmitting state and a light blocking state, for each of the left and the right shutters in synchronization with the timing with which the infrared rays are received by the infrared ray receiving unit. In the following sections, the process to switch between the light transmitting state and the light blocking state of the shutters will be explained.

As shown in FIG. 2B, each of the shutters includes an entering-side polarizing plate and an exiting-side polarizing plate and further includes a liquid crystal layer between the entering-side polarizing plate and the exiting-side polarizing plate. The entering-side polarizing plate and the exiting-side polarizing plate are positioned orthogonal to each other as shown in FIG. 2B. In this situation, as shown in FIG. 2B, while the voltage is not applied ("OFF"), the light that has passed through the entering-side polarizing plate is rotated by 90 degrees due to an action of the liquid crystal layer and transmits through the exiting-side polarizing plate. In other words, the shutter is in the light transmitting state while the voltage is not being applied.

On the contrary, as shown in FIG. 2B, while the voltage is being applied ("ON"), because the polarization rotation action of the liquid crystal molecules in the liquid crystal layer is lost, the light that has passed through the entering-side polarizing plate is blocked by the exiting-side polarizing plate. In other words, the shutter is in the light blocking state while the voltage is being applied.

In this arrangement, for example, the infrared ray emitting unit emits infrared rays during the time period when a left-eye image is being displayed on the monitor. The infrared ray receiving unit applies no voltage to the left-eye shutter and applies a voltage to the right-eye shutter, during the time period when receiving the infrared rays. As a result, as shown in FIG. 2A, the right-eye shutter is in the light blocking state, whereas the left-eye shutter is in the light transmitting state, so that the left-eye image goes into the left eye of the viewer. On the contrary, the infrared ray emitting unit stops emitting infrared rays during the time period when a right-eye image is being displayed on the monitor. The infrared ray receiving unit applies no voltage to the right-eye shutter and applies a voltage to the left-eye shutter, during the time period when receiving no infrared rays. As a result, the left-eye shutter is in the light blocking state, whereas the right-eye shutter is in the light transmitting state, so that the right-eye image goes into the right eye of the viewer. In this manner, the stereoscopic display monitor shown in FIGS. 2A and 2B displays the images capable of providing the viewer with a stereoscopic view, by switching the images displayed by the monitor and the state of the shutters in conjunction with one another. Instead of the shutter method described above, a monitor that uses a polarized-glasses method is also known as a stereoscopic display monitor that is capable of providing a stereoscopic view of two-eye disparity images.

Further, examples of stereoscopic display monitors that were put in practical use in recent years include an apparatus that enables a glass-free viewer to have a stereoscopic view of multiple-eye disparity images such as nine-eye disparity images by using a light beam controller such as a lenticular lens. Such a stereoscopic display monitor is configured to enable the viewer to have a stereoscopic view using a binocular disparity and further enables the viewer to have a stereoscopic view using a motion disparity, by which the viewed pictures also change in accordance with shifting of the viewpoints of the viewer.

Figure 3:
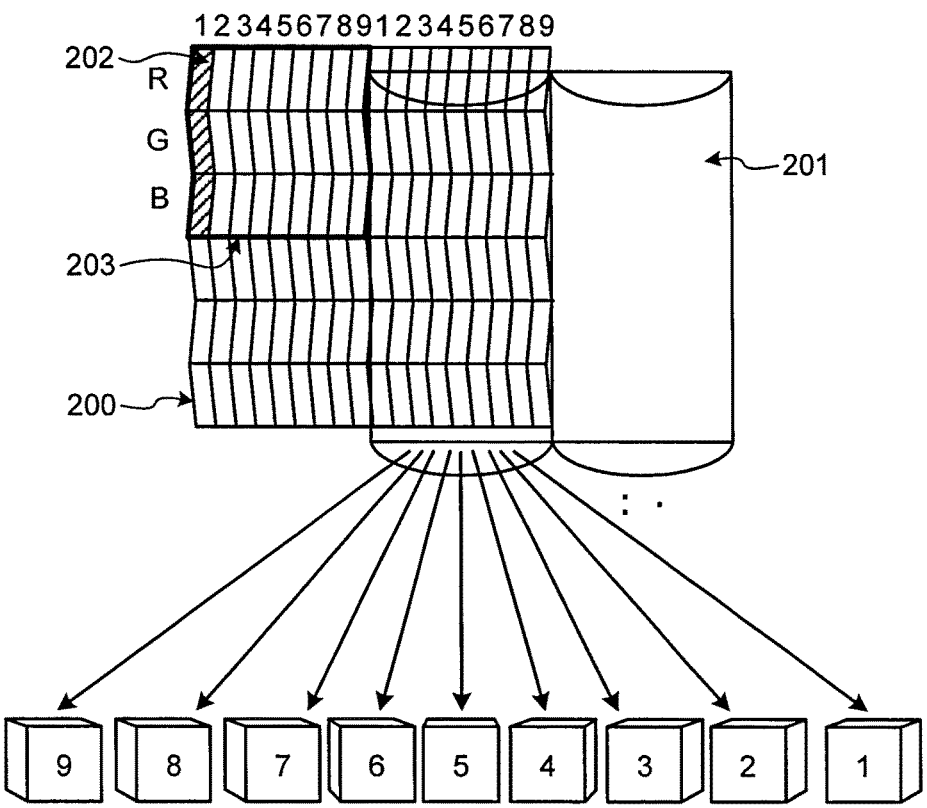
FIG. 3 is a drawing for explaining an example of a stereoscopic display monitor that realizes a stereoscopic display by using nine-eye disparity images.

FIG. 3 is a drawing for explaining an example of a stereoscopic display monitor that realizes a stereoscopic display by using nine-eye disparity images. The stereoscopic display monitor shown in FIG. 3 is configured so that a light beam controller is disposed to the front of a flat-shaped display surface 200 such as a liquid crystal panel. For example, the stereoscopic display monitor shown in FIG. 3 is configured so that, as the light beam controller, a vertical lenticular sheet 201 of which the optical openings extend in vertical directions is pasted onto the front of the display surface 200.

As shown in FIG. 3, on the display surface 200, pixels 202 are arranged in a matrix formation, each of the pixels 202 having a length-width ratio of 3:1 and having three sub-pixels for red (R), green (G), and blue (B) arranged in the lengthwise direction. The stereoscopic display monitor shown in FIG. 3 is configured to convert nine-eye disparity images made up of nine images into intermediate images that are arranged in a predetermined format (e.g., in a lattice pattern) and outputs the conversion result to the display surface 200. In other words, the stereoscopic display monitor shown in FIG. 3 outputs nine pixels in mutually the same position in the nine-eye disparity images, while assigning those pixels to nine columns of the pixels 202, respectively. The nine columns of pixels 202 form a unit pixel group 203 that simultaneously displays nine images having mutually-different viewpoint positions.

The nine-eye disparity images that are simultaneously output as the unit pixel group 203 from the display surface 200 are emitted as parallel beams by, for example, a Light Emitting Diode (LED) backlight and are further emitted in multiple directions by the vertical lenticular sheet 201. Because the light beams of the pixels in the nine-eye disparity images are emitted in the multiple directions, the light beams entering the right eye and the left eye of the viewer change in conjunction with the position of the viewer (the viewpoint position). In other words, depending on the angle at which the viewer views the image, the disparity angles of the disparity image entering the right eye and the disparity image entering the left eye vary. As a result, the viewer is able to have a stereoscopic view of the target of an image-taking process (hereinafter, "image-taking target") at each of the nine positions shown in FIG. 3, for example. Further, for example, the viewer is able to have a stereoscopic view at the position "5" shown in FIG. 3 while facing the image-taking target straight on and is able to have a stereoscopic view at each of the positions other than the position "5" shown in FIG. 3 while the direction of the image-taking target is varied. The stereoscopic display monitor shown in FIG. 3 is merely an example. The stereoscopic display monitor that displays nine-eye disparity images may be configured with liquid crystal stripes arranged in a widthwise direction such as "R, R, R, . . . G, G, G, . . . B, B, B, . . . " as shown in FIG. 3 or may be configured with liquid crystal stripes arranged in a lengthwise direction such as "R, G, B, R, G, B, . . . ". Further, the stereoscopic display monitor shown in FIG. 3 may be realized with a lengthwise lens method where the lenticular sheet is positioned vertically as shown in FIG. 3 or may be realized with a diagonal lens method where the lenticular sheet is positioned diagonally.

The exemplary configuration of the image processing system 1 according to the first embodiment has thus been explained briefly. The application of the image processing system 1 described above is not limited to the situation where the PACS is introduced. For example, it is possible to apply the image processing system 1 similarly to a situation where an electronic medical record system that manages electronic medical records to which medical images are attached is introduced. In that situation, the image storing apparatus 120 is configured as a database storing therein the electronic medical records. Further, it is acceptable to apply the image processing system 1 similarly to a situation where, for example, a Hospital Information System (HIS), or a Radiology Information System (RIS) is introduced. Further, the image processing system 1 is not limited to the exemplary configuration described above. The functions of the apparatuses and the distribution of the functions among the apparatuses may be changed as necessary according to modes of operation thereof.

Figure 4:
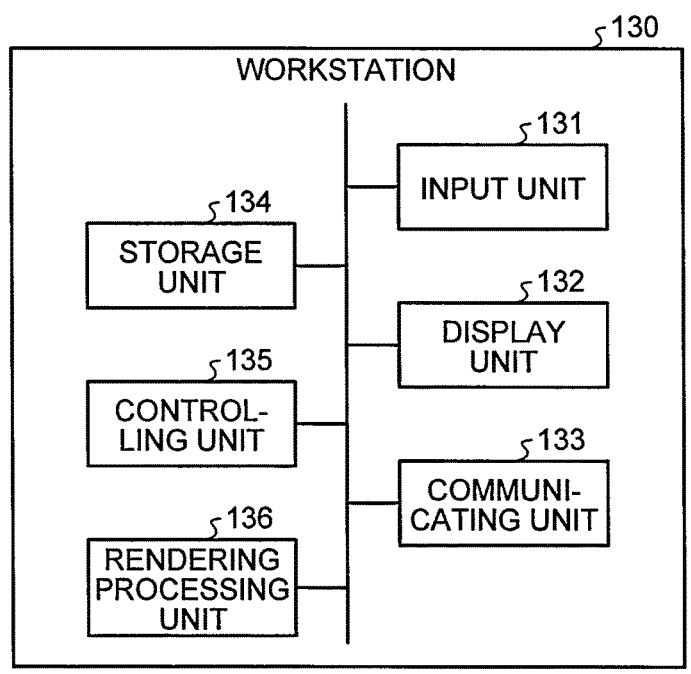
FIG. 4 is a drawing for explaining an exemplary configuration of a workstation according to the first embodiment.

Next, an exemplary configuration of the workstation according to the first embodiment will be explained, with reference to FIG. 4. FIG. 4 is a drawing for explaining the exemplary configuration of the workstation according to the first embodiment. In the following sections, the term "a group of disparity images" refers to a group of images that realize a stereoscopic view and are generated by performing a volume rendering process on volume data. Further, the term "disparity image" refers to each of the individual images constituting "a group of disparity images". In other words, "a group of disparity images" is made up of a plurality of "disparity images" having mutually-different viewpoint positions.

The workstation 130 according to the first embodiment is a high-performance computer suitable for performing image processing processes and the like. As shown in FIG. 4, the workstation 130 includes an input unit 131, a display unit 132, a communicating unit 133, a storage unit 134, a controlling unit 135, and a rendering processing unit 136. The explanation below is based on an example in which the workstation 130 is a high-performance computer suitable for performing image processing processes and the like; however, the exemplary embodiments are not limited to this example. The workstation 130 may be an arbitrary information processing apparatus. For example, the workstation 130 may be an arbitrary personal computer.

The input unit 131 is configured with a mouse, a keyboard, a trackball and/or the like and receives inputs of various types of operations performed on the workstation 130 from the operator. More specifically, the input unit 131 according to the first embodiment receives an input of information used for obtaining the volume data serving as a target of a rendering process, from the image storing apparatus 120. For example, the input unit 131 receives an input of a patient ID, a medical examination ID, an apparatus ID, a series ID, and/or the like. Further, the input unit 131 according to the first embodiment receives an input of conditions related to the rendering process (hereinafter, "rendering conditions").

The display unit 132 is a liquid crystal panel or the like that serves as the stereoscopic display monitor and is configured to display various types of information. More specifically, the display unit 132 according to the first embodiment displays a Graphical User Interface (GUI) used for receiving various types of operations from the operator, the group of disparity images, and the like. The communicating unit 133 is a Network Interface Card (NIC) or the like and is configured to communicate with other apparatuses.

The storage unit 134 is a hard disk, a semiconductor memory element, or the like and is configured to store therein various types of information. More specifically, the storage unit 134 according to the first embodiment stores therein the volume data obtained from the image storing apparatus 120 via the communicating unit 133. Further, the storage unit 134 according to the first embodiment stores therein volume data on which a rendering process is being performed, a group of disparity images generated by performing a rendering process, images to be displayed two-dimensionally, and the like.

The controlling unit 135 is an electronic circuit such as a Central Processing Unit (CPU) or a Micro Processing Unit (MPU), or an integrated circuit such as an Application Specific Integrated Circuit (ASIC) or a Field Programmable Gate Array (FPGA) and is configured to exercise overall control of the workstation 130.

For example, the controlling unit 135 according to the first embodiment controls the display of the GUI or the display of the group of disparity images on the display unit 132. As another example, the controlling unit 135 controls the transmissions and the receptions of the volume data and the group of disparity images that are transmitted to and received from the image storing apparatus 120 via the communicating unit 133. As yet another example, the controlling unit 135 controls the rendering process performed by the rendering processing unit 136. As yet another example, the controlling unit 135 controls the reading of the volume data from the storage unit 134 and the storing of the group of disparity images into the storage unit 134.

Under the control of the controlling unit 135, the rendering processing unit 136 generates the group of disparity images by performing various types of rendering processes on the volume data obtained from the image storing apparatus 120. More specifically, the rendering processing unit 136 according to the first embodiment reads the volume data from the storage unit 134 and first performs a pre-processing process on the read volume data. Subsequently, the rendering processing unit 136 generates the group of disparity images by performing a volume rendering process on the pre-processed volume data. After that, the rendering processing unit 136 generates a two-dimensional image in which various types of information (a scale mark, the patient's name, tested items, and the like) are rendered and superimposes the generated two-dimensional image onto each member of the group of disparity images so as to generate output-purpose two-dimensional images. Further, the rendering processing unit 136 stores the generated group of disparity images and the output-purpose two-dimensional images into the storage unit 134. In the first embodiment, the "rendering process" refers to the entirety of the image processing performed on the volume data. The "volume rendering process" refers to a part of the rendering process and is a process to generate the two-dimensional images reflecting three-dimensional information. Medical images generated by performing a rendering process may correspond to, for example, disparity images.

Figure 5:
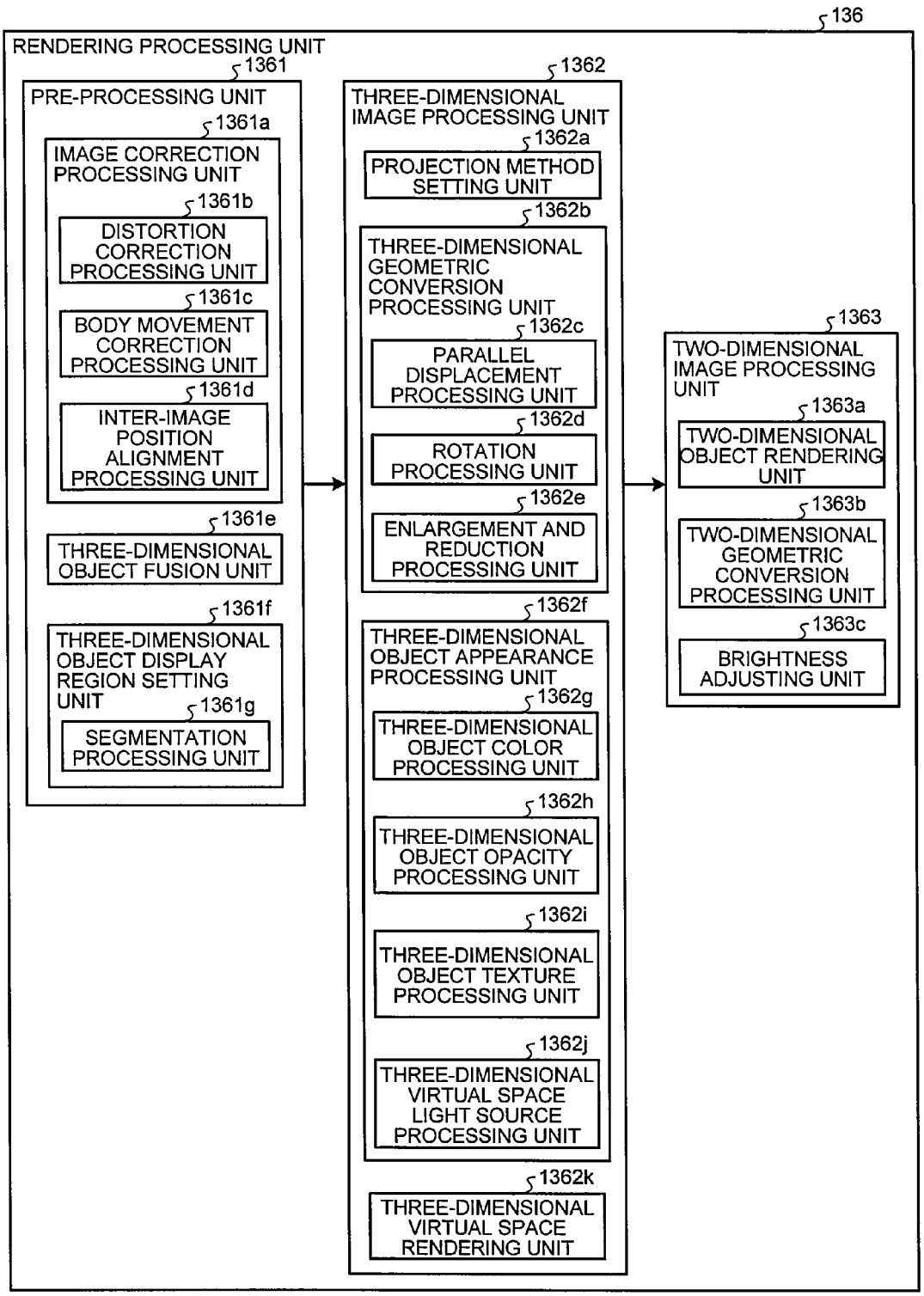
FIG. 5 is a drawing for explaining an exemplary configuration of a rendering processing unit shown in FIG. 4.

FIG. 5 is a drawing for explaining an exemplary configuration of the rendering processing unit shown in FIG. 4. As shown in FIG. 5, the rendering processing unit 136 includes a pre-processing unit 1361, a three-dimensional image processing unit 1362, and a two-dimensional image processing unit 1363. The pre-processing unit 1361 performs the pre-processing process on the volume data. The three-dimensional image processing unit 1362 generates the group of disparity images from the pre-processed volume data. The two-dimensional image processing unit 1363 generates the output-purpose two-dimensional images obtained by superimposing the various types of information on the group of disparity images. These units will be explained one by one below.

The pre-processing unit 1361 is a processing unit that performs various types of pre-processing processes before performing the rendering process on the volume data and includes an image correction processing unit 1361a, a three-dimensional object fusion unit 1361e, and a three-dimensional object display region setting unit 1361f.

The image correction processing unit 1361a is a processing unit that performs an image correction process, when two types of volume data are processed as one piece of volume data and includes, as shown in FIG. 5, a distortion correction processing unit 1361b, a body movement correction processing unit 1361c, and an inter-image position alignment processing unit 1361d. For example, when volume data of a PET image and volume data of an X-ray CT image that are generated by a PET-CT apparatus are to be processed as one piece of volume data, the image correction processing unit 1361a performs an image correction process. As another example, when volume data of a T1-weighted image and volume data of a T2-weighted image that are generated by an MRI apparatus are to be processed as one piece of volume data, the image correction processing unit 1361a performs an image correction process.

Further, for each piece of volume data, the distortion correction processing unit 1361b corrects a distortion in the data caused by acquiring conditions used during a data acquiring process performed by the medical image diagnosis apparatus 110. Further, the body movement correction processing unit 1361c corrects movements caused by body movements of the subject that occurred during a data acquisition period used for generating each piece of volume data. The inter-image position alignment processing unit 1361d performs a position alignment (registration) process that uses, for example, a cross-correlation method, on two pieces of volume data on which the correction processes have been performed by the distortion correction processing unit 1361b and the body movement correction processing unit 1361c.

The three-dimensional object fusion unit 1361e fuses together the plurality of pieces of volume data on which the position alignment process has been performed by the inter-image position alignment processing unit 1361d. The processes performed by the image correction processing unit 1361a and the three-dimensional object fusion unit 1361e are omitted if the rendering process is performed on a single piece of volume data.

The three-dimensional object display region setting unit 1361f is a processing unit that sets a display region corresponding to a display target organ specified by the operator and includes a segmentation processing unit 1361g. The segmentation processing unit 1361g is a processing unit that extracts an organ specified by the operator such as the heart, a lung, or a blood vessel, by using, for example, a region growing method based on pixel values (voxel values) of the volume data.

If no display target organ was specified by the operator, the segmentation processing unit 1361g does not perform the segmentation process. As another example, if a plurality of display target organs are specified by the operator, the segmentation processing unit 1361g extracts the corresponding plurality of organs. The process performed by the segmentation processing unit 1361g may be performed again, in response to a fine-adjustment request from the operator who has observed the rendering images.

The three-dimensional image processing unit 1362 performs the volume rendering process on the pre-processed volume data processed by the pre-processing unit 1361. As processing units that perform the volume rendering process, the three-dimensional image processing unit 1362 includes a projection method setting unit 1362a, a three-dimensional geometric conversion processing unit 1362b, a three-dimensional object appearance processing unit 1362f, and a three-dimensional virtual space rendering unit 1362k.

The projection method setting unit 1362a determines a projection method used for generating the group of disparity images. For example, the projection method setting unit 1362a determines whether the volume rendering process is to be performed by using a parallel projection method or is to be performed by using a perspective projection method.

The three-dimensional geometric conversion processing unit 1362b is a processing unit that determines information used for three-dimensionally and geometrically converting the volume data on which the volume rendering process is performed and includes a parallel displacement processing unit 1362c, a rotation processing unit 1362d, and an enlargement and reduction processing unit 1362e. The parallel displacement processing unit 1362c is a processing unit that, when the viewpoint positions used in the volume rendering process are moved in a parallel displacement, determines a displacement amount by which the volume data should be moved in a parallel displacement. The rotation processing unit 1362d is a processing unit that, when the viewpoint positions used in the volume rendering process are moved in a rotational shift, determines a shift amount by which the volume data should be moved in a rotational shift. The enlargement and reduction processing unit 1362e is a processing unit that, when an enlargement or a reduction of the group of disparity images is requested, determines an enlargement ratio or a reduction ratio of the volume data.

The three-dimensional object appearance processing unit 1362f includes a three-dimensional object color processing unit 1362g, a three-dimensional object opacity processing unit 1362h, a three-dimensional object texture processing unit 1362i, and a three-dimensional virtual space light source processing unit 1362j. By using these processing units, the three-dimensional object appearance processing unit 1362f performs a process to determine a display state of the group of disparity images to be displayed, according to, for example, a request from the operator.

The three-dimensional object color processing unit 1362g is a processing unit that determines the colors applied to the regions resulting from the segmentation process within the volume data. The three-dimensional object opacity processing unit 1362h is a processing unit that determines opacity of each of the voxels constituting the regions resulting from the segmentation process within the volume data. A region positioned behind a region of which the opacity is set to "100%" in the volume data will not be rendered in the group of disparity images. As another example, a region of which the opacity is set to "0%" in the volume data will not be rendered in the group of disparity images.

The three-dimensional object texture processing unit 1362i is a processing unit that adjusts the texture that is used when each of the regions is rendered, by determining the texture of each of the regions resulting from the segmentation process within the volume data. The three-dimensional virtual space light source processing unit 1362j is a processing unit that determines a position of a virtual light source to be placed in a three-dimensional virtual space and a type of the virtual light source, when the volume rendering process is performed on the volume data. Examples of types of the virtual light source include a light source that radiates parallel light beams from an infinite distance and a light source that radiates radial light beams from a viewpoint.

The three-dimensional virtual space rendering unit 1362k generates the group of disparity images by performing the volume rendering process on the volume data. When performing the volume rendering process, the three-dimensional virtual space rendering unit 1362k uses, as necessary, the various types of information determined by the projection method setting unit 1362a, the three-dimensional geometric conversion processing unit 1362b, and the three-dimensional object appearance processing unit 1362f.

In this situation, the volume rendering process performed by the three-dimensional virtual space rendering unit 1362k is performed according to the rendering conditions. An example of the rendering conditions is the "parallel projection method" or the "perspective projection method". Another example of the rendering conditions is "a reference viewpoint position and the disparity angle". Other examples of the rendering conditions include "a parallel displacement of the viewpoint position", "a rotational shift of the viewpoint position", "an enlargement of the group of disparity images", and "a reduction of the group of disparity images". Further examples of the rendering conditions include "the colors to be applied", "the opacity", "the texture", "the position of the virtual light source", and "the type of the virtual light source". These rendering conditions may be received from the operator via the input unit 131 or may be specified in initial settings. In either situation, the three-dimensional virtual space rendering unit 1362k receives the rendering conditions from the controlling unit 135 and performs the volume rendering process on the volume data according to the received rendering conditions. Further, in that situation, because the projection method setting unit 1362a, the three-dimensional geometric conversion processing unit 1362b, and the three-dimensional object appearance processing unit 1362f described above determine the required various types of information according to the rendering conditions, the three-dimensional virtual space rendering unit 1362k generates the group of disparity images by using those various types of information that were determined.

Figure 6:
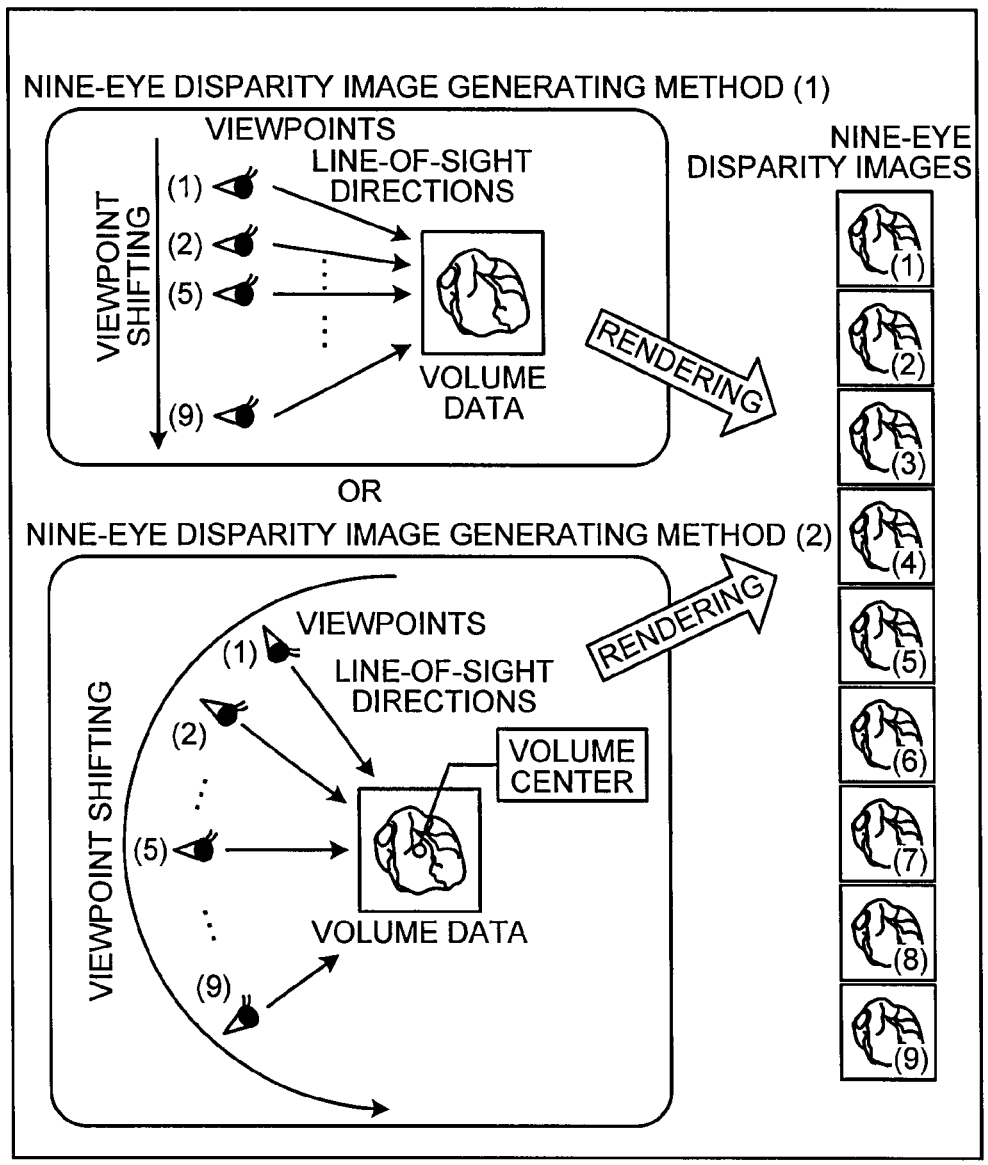
FIG. 6 is a drawing for explaining an example of a volume rendering process according to the first embodiment.

FIG. 6 is a drawing for explaining an example of the volume rendering process according to the first embodiment. For example, let us discuss a situation in which, as shown in "nine-eye disparity image generating method (1)" in FIG. 6, the three-dimensional virtual space rendering unit 1362k receives, as rendering conditions, the parallel projection method and further receives viewpoint position (5) used as a reference point and a disparity angle "1 degree". In that situation, the three-dimensional virtual space rendering unit 1362k uses the parallel projection method and generates nine disparity images in which the disparity angles (the angles between the line-of-sight directions) are different by 1 degree each, by moving the viewpoint position to positions (1) to (9) in the manner of a parallel displacement, so that the disparity angles are mutually different by "1 degree". When implementing the parallel projection method, the three-dimensional virtual space rendering unit 1362k sets a light source that radiates parallel light beams from an infinite distance along the line-of-sight directions.

As another example, let us discuss a situation in which, as shown in "nine-eye disparity image generating method (2)" in FIG. 6, the three-dimensional virtual space rendering unit 1362k receives, as rendering conditions, the perspective projection method and further receives viewpoint position (5) used as a reference point and a disparity angle "1 degree". In that situation, the three-dimensional virtual space rendering unit 1362k uses the perspective projection method and generates nine disparity images in which the disparity angles are different by 1 degree each, by moving the viewpoint position to positions (1) to (9) in the manner of a rotational shift, so that the disparity angles are mutually different by "1 degree" while being centered on the center (the gravity point) of the volume data. When implementing the perspective projection method, the three-dimensional virtual space rendering unit 1362k sets, at each of the viewpoints, a point light source or an area light source that three-dimensionally and radially radiates light being centered on the line-of-sight direction. Alternatively, when the perspective projection method is implemented, it is acceptable to move viewpoints (1) to (9) in the manner of a parallel displacement, depending on rendering conditions being used.

As yet another example, the three-dimensional virtual space rendering unit 1362k may perform a volume rendering process while using the parallel projection method and the perspective projection method together, by setting a light source that two-dimensionally and radially radiates light being centered on the line-of-sight direction with respect to the lengthwise direction of the volume rendering image to be displayed and that radiates parallel light beams from an infinite distance along the line-of-sight direction with respect to the widthwise direction of the volume rendering image to be displayed.

The nine disparity images generated in this manner constitute the group of disparity images. In the first embodiment, for example, the nine disparity images are converted, by the controlling unit 135, into the intermediate images that are arranged in the predetermined format (e.g., in a lattice pattern), and the conversion result is output to the display unit 132 serving as the stereoscopic display monitor. As a result, the operator of the workstation 130 is able to perform the operation to generate a group of disparity images, while viewing the medical images that are capable of providing a stereoscopic view and are being displayed on the stereoscopic display monitor.

In the example illustrated in FIG. 6, the situation is explained where the projection method, the reference viewpoint position, and the disparity angle are received as the rendering conditions; however, in other situations where other conditions are received as the rendering conditions, the three-dimensional virtual space rendering unit 1362k similarly generates a group of disparity images, while ensuring that each of the rendering conditions is reflected.

Further, the three-dimensional virtual space rendering unit 1362k not only performs the volume rendering process, but also reconstructs a planar image on an arbitrary plane (e.g., an axial plane, a sagittal plane, a coronal plane). For example, the three-dimensional virtual space rendering unit 1362k reconstructs a Multi Planar Reconstruction (MPR) image from the volume data by implementing an MPR method. In addition, the three-dimensional virtual space rendering unit 1362k also has a function of performing a "curved MPR" and a function of performing an "intensity projection".

After that, each member of the group of disparity images generated by the three-dimensional image processing unit 1362 from the volume data is used as an underlay. By superimposing an overlay in which the various types of information (a scale mark, the patient's name, tested items, and the like) are rendered onto the underlay images, the output-purpose two-dimensional images are obtained. The two-dimensional image processing unit 1363 is a processing unit that generates the output-purpose two-dimensional images by performing an image processing process on the overlay and underlay images. As shown in FIG. 5, the two-dimensional image processing unit 1363 includes a two-dimensional object rendering unit 1363a, a two-dimensional geometric conversion processing unit 1363b, and a brightness adjusting unit 1363c. For example, to reduce the load required by the generating process of the output-purpose two-dimensional images, the two-dimensional image processing unit 1363 generates nine output-purpose two-dimensional images by superimposing one overlay onto each of the nine disparity images (the underlay images).

The two-dimensional object rendering unit 1363a is a processing unit that renders the various types of information rendered in the overlay. The two-dimensional geometric conversion processing unit 1363b is a processing unit that performs a parallel displacement process or a rotational shift process on the positions of the various types of information rendered in the overlay and applies an enlargement process or a reduction process on the various types of information rendered in the overlay.

The brightness adjusting unit 1363c is a processing unit that performs a brightness conversion process and is a processing unit that adjusts brightness levels of the overlay and underlay images, according to parameters used for the image processing process such as the gradation of the stereoscopic display monitor at an output destination, a Window Width (WW), and a Window Level (WL).

The output-purpose two-dimensional images generated in this manner are temporarily stored into the storage unit 134 by, for example, the controlling unit 135. After that, the output-purpose two-dimensional images are sent to the image storing apparatus 120 via the communicating unit 133. For example, the terminal apparatus 140 obtains the output-purpose two-dimensional images from the image storing apparatus 120 and converts the obtained images into the intermediate images arranged in the predetermined format (e.g., in a lattice pattern), before having the images displayed on the stereoscopic display monitor. As a result, a medical doctor or a laboratory technician who is the viewer is able to view the medical images that are capable of providing a stereoscopic view, while the various types of information (the scale mark, the patient's name, the tested items, and the like) are rendered therein.

The exemplary configurations of the image processing system 1 and the workstation 130 according of the first embodiment have thus been explained. As a result of the processes performed by the controlling unit 135 explained in detail below, the workstation 130 according to the first embodiment configured as described above makes it possible to easily view the images even when a plurality of images corresponding to mutually-different time phases are superimposed together. More specifically, the workstation 130 according to the first embodiment causes regions of interest each of which is included in a different one of a plurality of three-dimensional images corresponding to mutually-different time phases to be displayed in mutually-different display formats.

Next, a problem that arises when a plurality of three-dimensional images corresponding to mutually-different time phases are superimposed together and viewed will be explained. For example, when three-dimensional images are displayed on a monitor capable of providing a stereoscopic view, the viewer is able to view a site of interest in further detail, and the level of precision in diagnosis processes is expected to improve. For example, when assessing the effect of a tumor treatment using an anti-cancer agent or a radiation therapy, the viewer is able to stereoscopically view the tumor and assess the effect of the treatment. However, it is difficult for the viewer to understand the degree by which a tumor has got smaller when three-dimensional images before and after the treatment are displayed separately. Even if the three-dimensional images before and after the treatment are displayed while being superimposed together so as to enable the viewer to observe the changes in the size and the shape of the tumor, simply superimposing the images together only causes the images of the tumor to overlap each other, and it is still difficult to observe the changes in the size and the shape of the tumor. Even in this kind of situation, the workstation 130 according to the first embodiment makes it possible to easily observe the changes in the size and the shape of the tumor.

Figure 7:
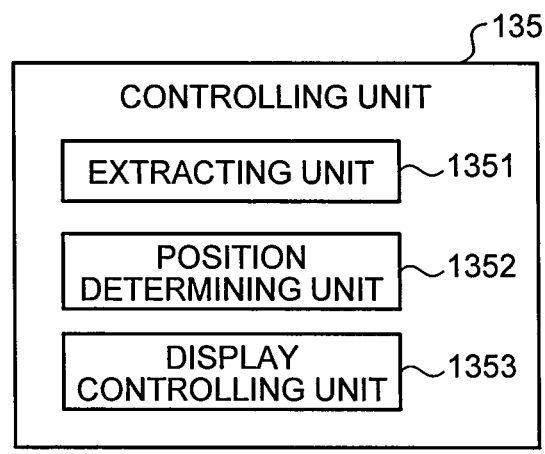
FIG. 7 is a drawing for explaining an exemplary configuration of a controlling unit according to the first embodiment.

FIG. 7 is a drawing for explaining an exemplary configuration of the controlling unit 135 according to the first embodiment. As shown in FIG. 7, the controlling unit 135 includes an extracting unit 1351, a position determining unit 1352, and a display controlling unit 1353. The extracting unit 1351 is configured to extract mutually the same region of interest from each of a plurality of pieces of three-dimensional image data corresponding to mutually-different time phases. More specifically, the extracting unit 1351 extracts the region of interest such as a tumor, from each of the plurality of pieces of volume data corresponding to the mutually-different time phases and being stored in the storage unit 134. For example, the extracting unit 1351 extracts the region of interest by using a region growing method, a threshold value method, a Computer Assisted Diagnosis (CAD) system, or the like.

FIG. 8 contains drawings for explaining an example of a process performed by the extracting unit 1351 according to the first embodiment. FIG. 8 illustrates an example in which a region of interest is extracted from each of pieces of volume data taken before and after treatment of liver cancer, the pieces of volume data being obtained by using an X-ray CT apparatus. Further, although the region of interest is schematically illustrated (as a sphere) in FIG. 8, each region of interest has a unique shape in actuality. For example, by implementing a region growing method that uses CT values, the extracting unit 1351 extracts, as a region of interest, a lesion site positioned in a region 300 within the volume data corresponding to <before treatment> shown in FIG. 8(A). In other words, the extracting unit 1351 extracts a Region Of Interest (ROI) 1 shown in the region 300, as shown in FIG. 8(B).

Similarly, by implementing the region growing method that uses CT values or the like, the extracting unit 1351 extracts, as a region of interest, a lesion site positioned in a region 301 within the volume data corresponding to <after treatment> shown in FIG. 8(A). In other words, the extracting unit 1351 extracts an ROI 2 shown in the region 301, as shown in FIG. 8(B). In the examples described above, the extractions of the regions of interest using the region growing method are explained; however, these are merely examples. It is acceptable to extract the regions of interest by using a threshold value method, a CAD system, or an analysis-purpose application. Also, in the examples described above, the three-dimensional image data taken by the X-ray CT apparatus is used; however, these are merely examples. It is acceptable to use three-dimensional image data taken by other modalities. In that situation, it is also possible to use mutually-different extracting methods in correspondence with mutually-different modalities.

In this situation, the operator is able to freely correct the regions of interest automatically extracted by the extracting unit 1351. For example, as shown in FIG. 8, when the extracting unit 1351 has extracted the ROI 1 and the ROI 2, the operator is able to reset any desired region as an ROI, by operating a cursor on each of the images corresponding to before and after the treatment. In another example, if no ROI has been extracted by the extracting unit 1351, the operator is also able to set an ROI. As for the setting of an ROI performed by the operator in these examples, the operator is able to reset the entirety of an ROI extracted by the extracting unit 1351 and is also able to partially correct an ROI extracted by the extracting unit 1351.

Returning to the description of FIG. 7, the position determining unit 1352 is configured to determine, on the basis of feature points included in the pieces of three-dimensional image data, a position used for superimposing together the regions of interest extracted by the extracting unit 1351 from the plurality of pieces of three-dimensional image data, in substantially the same position of the subject. More specifically, the position determining unit 1352 determines the position used for superimposing the regions of interest together, by three-dimensionally aligning the positions of the feature points included in the volume data.

Figure 9:
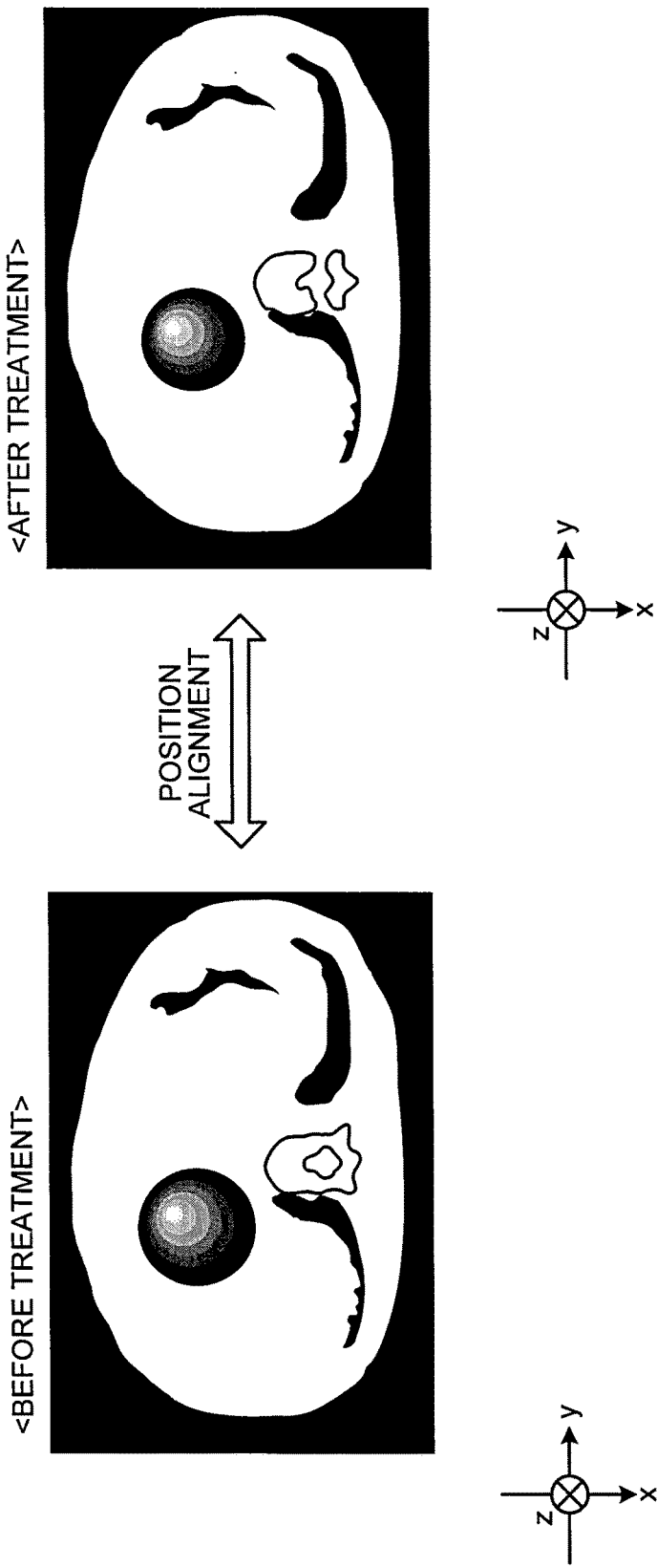
FIG. 9 is a drawing for explaining an example of a process performed by a position determining unit according to the first embodiment.

FIG. 9 is a drawing for explaining an example of a process performed by the position determining unit 1352 according to the first embodiment. FIG. 9 illustrates an example in which a position alignment process is performed on the pieces of volume data corresponding to before the treatment and after the treatment of the liver cancer shown in FIG. 8. For example, the position determining unit 1352 performs the position alignment process on the volume data corresponding to <before treatment> and the volume data corresponding to <after treatment> by performing a non-linear warping process.

In an example, as shown in FIG. 9 as <before treatment> and <after treatment>, the position determining unit 1352 sets an orthogonal coordinate system having three axes (an X-axis, a Y-axis, and a Z-axis) in each of the pieces of volume data. Further, the position determining unit 1352 divides each of the pieces of volume data into arbitrary smaller regions and performs the non-linear position alignment process on each of the smaller regions resulting from the dividing. In this situation, the position determining unit 1352 may perform the position alignment process using the non-linear warping process, by changing the shape of the volume data <before treatment> so as to match the volume data <after treatment> or by changing the shape of the volume data <after treatment> so as to match the volume data <before treatment>.

Further, the position determining unit 1352 is also able to perform a linear position alignment process such as a parallel displacement or a rotation, in addition to the non-linear warping process described above. For example, the position determining unit 1352 aligns the positions of the volume data <before treatment> and the volume data <after treatment> by extracting the spine or ribs rendered in the volume data <before treatment> and the volume data <after treatment> and three-dimensionally causing the extracted spines or the extracted ribs to overlap each other.

As a result of the process performed by the position determining unit 1352 described above, the workstation 130 according to the first embodiment accurately superimposes together the regions of interest included in the volume data <before treatment> and the volume data <after treatment>, by correcting the positional misalignment between the two pieces of volume data caused by respiratory volumes during the image taking processes and image taking postures. In the description above, the example is explained in which the entirety of each of the pieces of volume data is used; however, this is merely an example. It is acceptable to perform the position alignment process by using a part of each of the pieces of volume data. Further, the workstation 130 according to the first embodiment is able to perform a linear position alignment process and the position alignment process using the non-linear warping process in combination, as appropriate.

Returning to the description of FIG. 7, the display controlling unit 1353 changes the display format of each of the regions of interest extracted by the extracting unit 1351 from the plurality of pieces of three-dimensional image data so as to be mutually different and causes a superimposed image to be displayed by superimposing the regions of interest together in the position determined by the position determining unit 1352. More specifically, the display controlling unit 1353 first causes the rendering processing unit 136 to generate groups of disparity images corresponding to the mutually-different time phases, by performing a rendering process on each of the pieces of volume data of which the positions were aligned by the position determining unit 1352, so as to include the regions of interest and so that the line-of-sight directions are mutually the same. Subsequently, the display controlling unit 1353 changes colors and display modes of the regions of interest so as to be different between the groups of disparity images. After that, the display controlling unit 1353 causes the groups of disparity images to be displayed in mutually-different layers.

FIG. 10 is a drawing for explaining an example of a process performed by the display controlling unit 1353 according to the first embodiment. FIG. 10 illustrates an example in which groups of disparity images generated from the pieces of volume data <before treatment> and <after treatment> of the liver cancer shown in FIG. 8 are superimposed together. For example, as shown in FIG. 10, the display controlling unit 1353 causes a group of disparity images rendering the entire region to be generated from the volume data <after treatment> of which the position was aligned by the position determining unit 1352. Further, the display controlling unit 1353 causes a group of disparity images of the region corresponding to the region 301 to be generated from the volume data <before treatment> of which the position was aligned by the position determining unit 1352. The display controlling unit 1353 then causes such an image to be displayed that expresses the ROI 1 and the ROI 2 in mutually-different colors.

In an example, the display controlling unit 1353 causes such an image to be displayed that expresses the ROI 2 included in the volume data <after treatment> in "red" and expresses the ROI 1 included in the volume data <before treatment> in "blue". In this situation, with respect to each of the regions of interest extracted from the plurality of pieces of three-dimensional image data, the display controlling unit 1353 causes only a predetermined region thereof to be displayed. For example, as shown in FIG. 10, the display controlling unit 1353 causes such an image to be displayed in which the ROI 2 positioned inside is exposed, by arranging a part of the ROI 1 positioned on the outside so as not to be displayed when being superimposed. Although FIG. 10 illustrates an example in which one-eighth of the region of the ROI 1 is not displayed, the region that is not displayed may arbitrarily be set. For example, it is acceptable to arrange one-fourth of the ROI 1 so as not to be displayed. Further, the operator is able to arbitrarily change the part that is not displayed. For example, by operating a cursor on the image, the operator is able to arbitrarily change the part that is not displayed. In other words, the operator is able to arrange any arbitrary position of the ROI 2 to be exposed. Further, the display controlling unit 1353 is also capable of changing the opacity of each of the ROIs, in addition to the colors thereof.

Further, the display controlling unit 1353 is also capable of causing such ROIs to be displayed of which the colors and the three-dimensional amounts are changed on the basis of an amount of change in the volume, by comparing the volumes of the pieces of volume data corresponding to mutually-different time phases. For example, if the volume of the ROI 2 included in the volume data <after treatment> is "20%" or more smaller than the volume of the ROI 1 included in the volume data <before treatment>, the display controlling unit 1353 causes such an image to be displayed in which the ROI 1 is expressed in "yellow", whereas if "40%" or more smaller, the ROI 1 is expressed in "green". On the contrary, if the volume of the ROI 2 included in the volume data <after treatment> is "20%" or more larger than the volume of the ROI 1 included in the volume data <before treatment>, the display controlling unit 1353 causes such an image to be displayed in which the ROI 2 is expressed in "blue", whereas if "40%" or more larger, the ROI 2 is expressed in "purple". In other words, the display controlling unit 1353 displays the images from which the viewer is able to recognize at a glance how much the ROI has changed between <before treatment> and <after treatment>. As another example, the display controlling unit 1353 is capable of displaying an image of a tumor by changing the three-dimensional amount in such a manner that the tumor is displayed farther from the viewer if the size of the tumor has become smaller and is displayed closer to the viewer if the size of the tumor has become larger. If the volumes of the ROIs are equal (or if the difference in the volume is within a predetermined threshold value), the display controlling unit 1353 displays the ROIs without using any color.

The display controlling unit 1353 is capable of realizing a display by arbitrarily combining any of the display methods described above. As a result, the workstation 130 according to the first embodiment makes it possible for the viewer to recognize the changes in the ROI at a glance and to easily assess the effect of the treatment using an anti-cancer agent or a radiation therapy.

The color setting may be arbitrarily determined by the operator. For example, it is possible to set, in advance, the colors of each of the ROIs in an order based on the time series. Further, it is also possible to freely change, via the input unit 131, the color of each of the ROIs displayed by the display controlling unit 1353 on the display unit 132. For example, if the manner in which the regions of interest displayed on the display unit 132 overlap each other is unclear, it is possible to change the colors freely. Further, it is possible to configure the display controlling unit 1353 so as to be able to change the darkness, the contrast, the luminosity, and the like of the colors.

Figure 11:
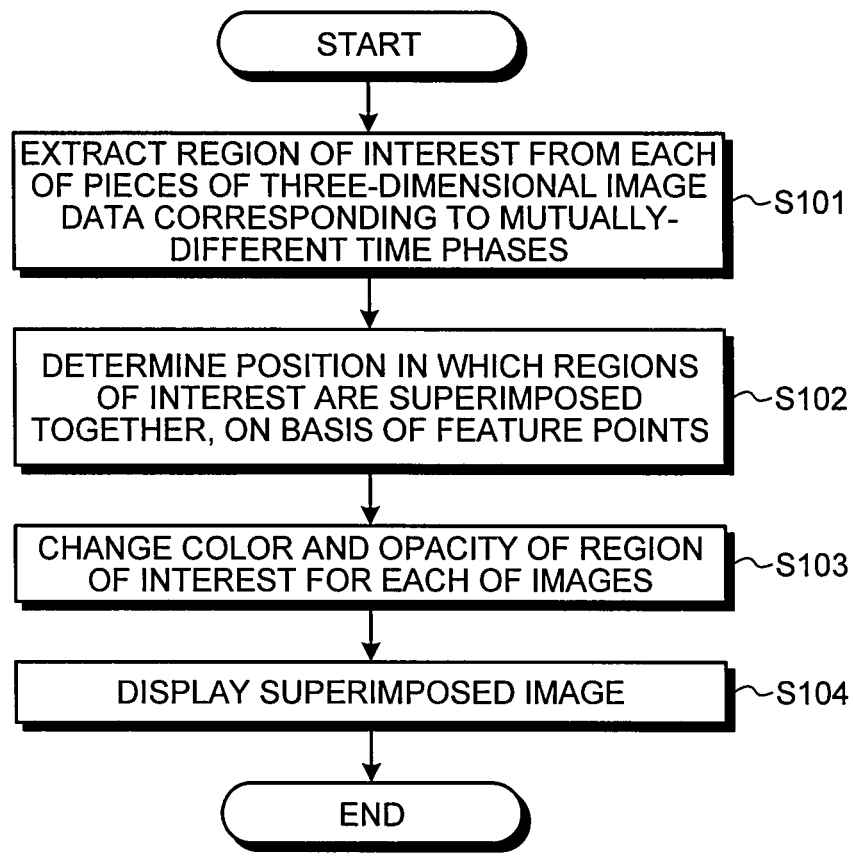
FIG. 11 is a flowchart of a procedure in a process performed by the workstation according to the first embodiment.

Next, processes performed by the workstation 130 according to the first embodiment will be explained, with reference to FIG. 11. FIG. 11 is a flowchart of a procedure in a process performed by the workstation 130 according to the first embodiment. As shown in FIG. 11, the workstation 130 according to the first embodiment is configured so that, when a command is executed to cause a plurality of images corresponding to mutually-different time phases to be displayed while being superimposed together, the extracting unit 1351 extracts a region of interest from each of a plurality of pieces of three-dimensional image data corresponding to the mutually-different time phases (step S101).

Further, the position determining unit 1352 determines, on basis of feature points included in the volume data, a position in which the regions of interest extracted by the extracting unit 1351 are to be superimposed together (step S102). After that, the display controlling unit 1353 changes the color and opacity of the region of interest for each of the images (step S103) and causes the display unit 132 to display a superimposed image obtained by superimposing together and displaying the images in mutually-different layers (step S104).

As explained above, according to the first embodiment, the extracting unit 1351 extracts mutually the same region of interest from each of the plurality of pieces of three-dimensional image data corresponding to the mutually-different time phases. After that, the position determining unit 1352 determines, on the basis of the feature points included in the three-dimensional image data, the position used for superimposing together the regions of interest extracted by the extracting unit 1351 from the plurality of pieces of three-dimensional image data, in substantially the same position. Further, the display controlling unit 1353 changes the display format of each of the regions of interest extracted by the extracting unit 1351 from the plurality of pieces of three-dimensional image data so as to be mutually different and causes the superimposed image to be displayed by superimposing the regions of interest together in the position determined by the position determining unit 1352. As a result, the workstation 130 according to the first embodiment is capable of displaying, on the same screen and in an identifiable manner, the regions of interest included in the pieces of three-dimensional image data taken in the mutually-different time phases. Thus, even if the plurality of images corresponding to the mutually-different time phases are superimposed together, the workstation 130 according to the first embodiment makes it possible to easily view the images.

Further, according to the first embodiment, with respect to each of the regions of interest extracted from the plurality of pieces of three-dimensional image data, the display controlling unit 1353 causes only the predetermined region thereof to be displayed. As a result, the workstation 130 according to the first embodiment enables the viewer to visually recognize, without fail, the region of interest positioned on the inside. Thus, even if the plurality of images corresponding to the mutually-different time phases are superimposed together, the workstation 130 according to the first embodiment makes it possible to easily view the images.

In the first embodiment described above, the example is explained in which the pieces of three-dimensional image data corresponding to the two time phases are superimposed together. In a second embodiment, an example will be explained in which pieces of three-dimensional image data corresponding to three or more time phases are superimposed together. The second embodiment uses the same configuration as that of the controlling unit 135 according to the first embodiment illustrated in FIG. 7. Thus, the second embodiment will be explained by referring to a controlling unit configured to cause the pieces of three-dimensional image data corresponding to the three or more time phases to be displayed while being superimposed together, as a display controlling unit 1353a. In other words, the display controlling unit 1353a is obtained by adding new processes to the display controlling unit 1353 illustrated in FIG. 7.

Figure 12:
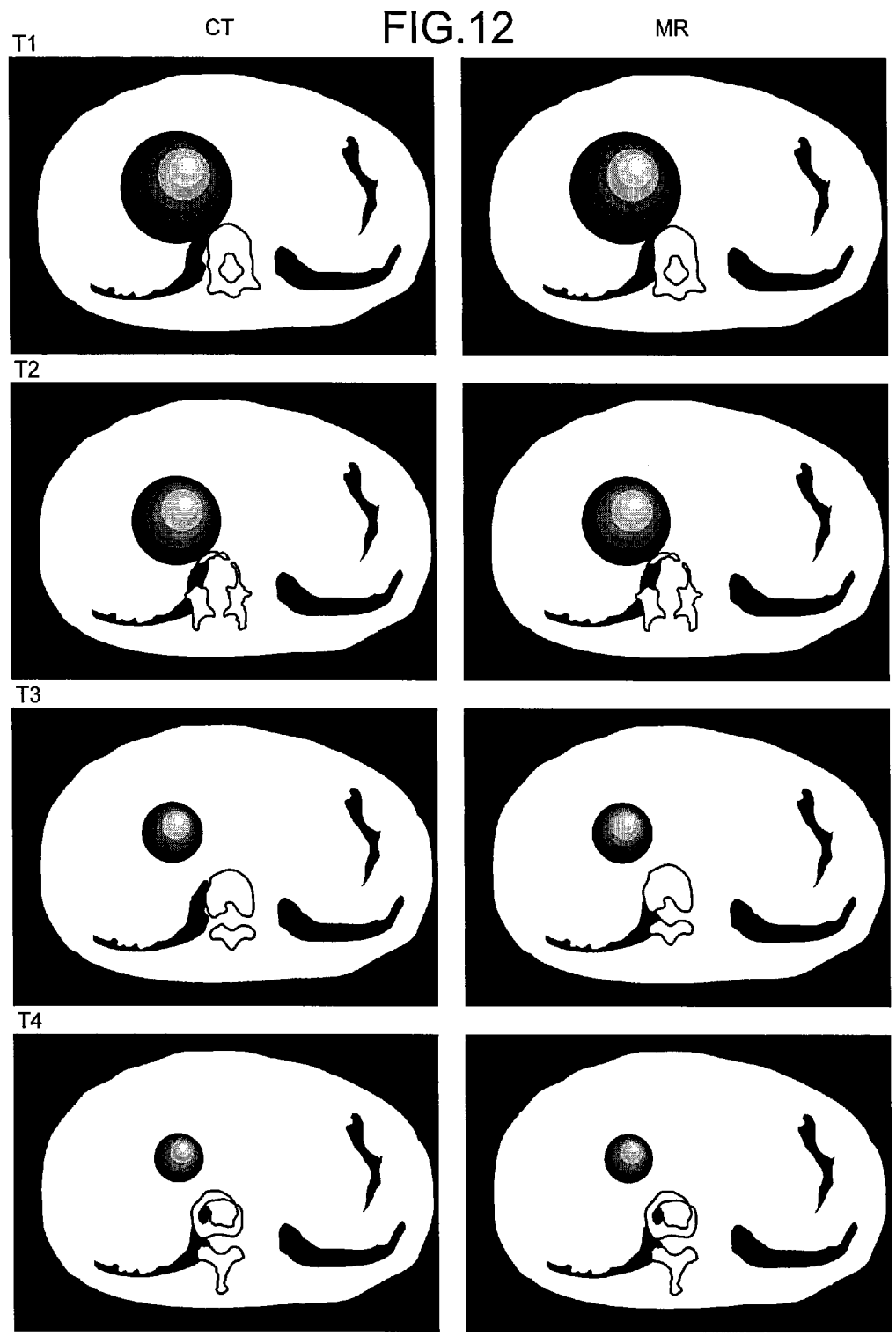
FIG. 12 is a drawing of an example of pieces of three-dimensional image data corresponding to three or more time phases according to a second embodiment.

The display controlling unit 1353a causes regions of interest included in the pieces of three-dimensional image data corresponding to the three or more time phases to be displayed in mutually-different display formats. More specifically, the display controlling unit 1353a causes the regions of interest extracted by the extracting unit 1351 from the pieces of volume data corresponding to the three or more time phases to be displayed in mutually-different colors. FIG. 12 is a drawing of an example of pieces of three-dimensional image data corresponding to three or more time phases according to the second embodiment. FIG. 12 illustrates perfusion images of the liver corresponding to mutually-different time phases. It should further be noted that FIG. 12 illustrates perfusion images taken by an X-ray CT apparatus and an MRI apparatus.

For example, as shown in FIG. 12, the controlling unit 135 according to the second embodiment causes pieces of three-dimensional image data including four time phases such as T1, T2, T3, and T4 to be displayed in the following manner: First, the extracting unit 1351 extracts a region of interest from each of the pieces of volume data corresponding to T1, T2, T3, and T4. For example, the extracting unit 1351 extracts an ROI 3 from the volume data corresponding to T1, extracts an ROI 4 from the volume data corresponding to T2, extracts an ROI 5 from the volume data corresponding to T3, and extracts an ROI 6 from the volume data corresponding to T4.

Further, the position determining unit 1352 performs a position alignment process on the pieces of volume data by performing a non-linear warping process, on the basis of feature points included in each of the pieces of volume data corresponding to T1, T2, T3, and T4. For example, the position determining unit 1352 changes the shape of each of the pieces of volume data corresponding to T1, T2, and T3, so as to match the piece of volume data corresponding to T4.

After that, the display controlling unit 1353a causes groups of disparity images to be generated by performing a rendering process on each of the pieces of volume data of which the positions were aligned by the position determining unit 1352, so as to include the regions of interest and so that the line-of-sight directions are mutually the same. Subsequently, the display controlling unit 1353a changes the colors of the regions of interest so as to be different between the groups of disparity images. After that, the display controlling unit 1353a causes the groups of disparity images to be displayed in mutually-different layers.

FIG. 13 is a drawing for explaining a first example of a process performed by the display controlling unit 1353a according to the second embodiment. FIG. 13 illustrates an example in which the groups of disparity images generated from the pieces of volume data corresponding to T1, T2, T3, and T4 shown in FIG. 12 are superimposed together. For example, the display controlling unit 1353a causes the ROIs 3 to 6 included in the pieces of volume data corresponding to T1, T2, T3, and T4 to be displayed in colors that are set in an order based on the time series, in such a manner that the region that is not displayed becomes larger as the volume increases.

This aspect will be further explained, with reference to FIG. 13. For example, the display controlling unit 1353a causes the ROI 3 to be displayed in "purple", the ROI 5 to be displayed in "blue", the ROI 4 to be displayed in "orange", and the ROI 6 to be displayed in "red". In this situation, as shown in FIG. 13, the display controlling unit 1353a causes such an image to be displayed in which, with respect to each of all the ROIs, a part of the ROI is not displayed so as to be partially exposed. As a result, the ROIs 3 to 6 displayed by the display controlling unit 1353a are displayed on the display unit 132 in such a manner that, as shown in FIG. 13, the viewer is able to easily understand the changes in the ROI for all of the time phases.

In another example, the display controlling unit 1353a is also capable of causing only the two regions of interest having the largest difference in the volume to be displayed, from among the regions of interest included in the pieces of three-dimensional image data corresponding to three or more time phases. FIG. 14 is a drawing for explaining a second example of a process performed by the display controlling unit 1353a according to the second embodiment. For example, as shown in FIG. 14, the display controlling unit 1353a extracts the ROI 3 and the ROI 6 having the largest difference in the volume from among the ROIs 3 to 6, changes the colors of the two extracted ROIs, and causes the display unit 132 to display a superimposed image in which a part of the ROI 3 is not displayed.

According to the second embodiment described above, the display controlling unit 1353a causes the regions of interest included in the pieces of three-dimensional image data corresponding to the three or more time phases to be displayed in such a manner that the regions of interest are identifiable from one another. As a result, the workstation 130 according to the second embodiment makes it possible to easily view the regions of interest realized by using the pieces of data that are in series chronologically. For example, the viewer is also able to assess the manner in which a tumor adheres, by observing shift amounts of the tumor while using the 4D data.

In the first and the second embodiments described above, the example is explained in which the regions of interest are extracted by using the region growing method based on the CT values in the X-ray CT images. In a third embodiment, an example will be explained in which regions of interest are extracted on the basis of information obtained from functional images. The third embodiment uses the same configuration as that of the controlling unit 135 according to the first embodiment illustrated in FIG. 7. Thus, the third embodiment will be explained by referring to a controlling unit configured to extract the regions of interest on the basis of the information obtained from the functional images as an extracting unit 1351a. In other words, the extracting unit 1351a is obtained by adding new processes to the extracting unit 1351 illustrated in FIG. 7.

The extracting unit 1351a extracts the regions of interest on the basis of information obtained from functional images and morphological images. In the following sections, an example will be explained in which the regions of interest are extracted by using PET images and CT images. FIG. 15 is a drawing for explaining an example of a process performed by the extracting unit 1351a according to the third embodiment. FIG. 15 illustrates an example in which a region of interest is extracted by using three-dimensional image data (a CT image and a PET image) taken by a PET-CT apparatus.

For example, as shown in FIG. 15, the extracting unit 1351a causes a fused image to be generated from a three-dimensional CT image and a three-dimensional PET image corresponding to one time phase and being stored in the storage unit 134. Further, from the generated fused image, the extracting unit 1351a extracts the position of a tumor in the three-dimensional CT image. Similarly, with respect to the three-dimensional image data corresponding to each of the other time phases, the extracting unit 1351a extracts a position of the tumor in a three-dimensional CT image, by fusing a PET image and the CT image together.

It is possible to extract a region of interest by using a PET image in the manner described above, not only when three-dimensional CT images corresponding to mutually-different time phases are superimposed together, but also when three-dimensional fused images corresponding to mutually-different time phases are superimposed together. When the fused images corresponding to the mutually-different time phases are superimposed together, the viewer is able to not only assess whether the tumor is malignant or not, but also spatially understand the manner in which the malignant tumor metastasizes.

Although the description above explained the example using the PET images, the exemplary embodiments are not limited to this example. For instance, it is also acceptable to use MR images or perfusion images.

In the third embodiment described above, the extracting unit 1351a extracts the regions of interest by using the three-dimensional PET images. As a result, the workstation 130 according to the third embodiment makes it possible to extract the regions of interest accurately.

The first, the second, and the third embodiments have thus been explained. The present disclosure, however, may be embodied in various forms other than the first, the second, and the third embodiments.

In the embodiments described above, the example using one region of interest is explained; however, the exemplary embodiments are not limited to this example. For instance, it is also acceptable to set a plurality of regions of interest.

In the embodiments described above, the example in which the tumor (the liver cancer) is used as the site of interest is explained; however, the exemplary embodiments are not limited to this example. For instance, it is also acceptable to use a region where signals are specifically increased by a contrast agent as a site of interest.

In the embodiments described above, the example using the spine or the ribs as the feature points for aligning the positions is explained; however, the exemplary embodiments are not limited to this example. For instance, it is also acceptable to use the gravity points of the regions of interest extracted by the extracting unit 1351 as the feature points. In that situation, the regions of interest are superimposed together by causing the gravity points of the regions of interest extracted by the extracting unit 1351 to overlap each other. For example, if the difference in the volume is large among the regions of interest extracted by the extracting unit 1351, it is possible to speed up the processing by performing the position alignment process while using the gravity points of the regions of interest.

In the embodiments described above, the example is explained in which the image is displayed by expressing the ROIs in the mutually-different colors and superimposing the ROIs together; however, the exemplary embodiments are not limited to this example. For instance, it is also acceptable to change the opacity for each of the ROIs.

For example, the display controlling unit 1353 may display an image while arranging the opacity of a region of interest having a large volume to be "50%" and the color thereof to be "red", while arranging the opacity of a region of interest having a small volume to be "100%" and the color thereof to be "blue". This aspect will be explained more specifically, with reference to FIG. 10. The display controlling unit 1353 compares the volume "$T_1$" of the ROI 1 included in the volume data before the treatment with the volume "$T_2$" of the ROI 2 included in the volume data after the treatment. Because "$T_1-T_2>0$" is satisfied, the display controlling unit 1353 causes the ROI 1 to be displayed with "opacity: 50%" and "color: red" and causes the ROI 2 to be displayed with "opacity: 100%" and "color: blue".

By displaying the images after changing the opacity of the image for each of the regions of interest in the manner described above, the workstation 130 according to the first embodiment makes it possible for the viewer to understand the whole picture of each of the regions of interest. Thus, even if the plurality of images corresponding to the mutually-different time phases are superimposed together, the workstation 130 makes it possible to easily view the images.

In the embodiments described above, the example is explained in which the tumor is rendered in each of the images corresponding to before the treatment and after the treatment; however, the exemplary embodiments are not limited to this example. For instance, another example is acceptable in which, while a tumor is rendered in an image corresponding to a current point in time, the image is compared with an image from the past. For example, the operator may set a region of interest in the image corresponding to the current point in time and in the image from the past and may cause a superimposed image to be displayed. The operator is thus able to have a metastasis state of the tumor displayed.

In the embodiments described above, the example is explained in which only the regions each including the region of interest are superimposed together; however, the exemplary embodiments are not limited to this example. For instance, it is also acceptable to superimpose the entirety of the images together.

In the embodiments described above, the example is explained in which the regions of interest each having a unique shape are superimposed together without applying any modification thereto; however, the exemplary embodiments are not limited to this example. For instance, it is also acceptable to superimpose the regions of interest together after changing the shapes thereof. In an example, it is acceptable to superimpose the regions of interest together, after changing the shapes of the regions of interest each having a unique shape to a standard shape. In this situation, examples of the standard shape include a sphere, a cube, and a rectangular parallelepiped. In an example, the display controlling unit 1353 displays an image by superimposing regions of interest together, after changing the shape of each of the plurality of regions of interest having been extracted by the extracting unit 1351 and corresponding to mutually-different time phases, to a sphere, a cube, a rectangular parallelepiped, or the like having a size that corresponds to the volume of the region of interest.

As a result, when the volume of the entire tumor has decreased due to necrosis occurring on the inside thereof, but it is difficult for the viewer to intuitively understand the amount of change, because the sites of interest are superimposed together after the shapes thereof are each changed into a sphere, a cube, a rectangular parallelepiped or the like that has the size corresponding to the volume thereof, this configuration makes it possible for the viewer to understand the amount of change more intuitively.

In the embodiments described above, the example is explained in which the workstation 130 displays the three-dimensional images being superimposed together; however, the exemplary embodiments are not limited to this example. For instance, another arrangement is also acceptable in which the medical image diagnosis apparatus 110 displays three-dimensional images being superimposed together. Yet another arrangement is also acceptable in which the medical image diagnosis apparatus 110 or the workstation 130 superimposes three-dimensional images together, whereas the terminal apparatus 140 displays the images.

In the embodiments described above, the terminal apparatus 140 is explained as being configured to, for example, display the medical images or the like obtained from the image storing apparatus 120; however, the exemplary embodiments are not limited to this example. For instance, another arrangement is acceptable in which the terminal apparatus 140 is directly connected to the medical image diagnosis apparatus 110 or the workstation 130.

In the embodiments described above, the example is explained in which the workstation 130 obtains the volume data from the image storing apparatus 120 and displays the superimposed image of the three-dimensional images obtained from the volume data; however, the exemplary embodiments are not limited to this example. For instance, another arrangement is also acceptable in which the workstation 130 obtains volume data from the medical image diagnosis apparatus 110 and displays a superimposed image of three-dimensional images obtained from the volume data.

In the embodiments described above, the example is explained in which the terminal apparatus 140 obtains the images from the image storing apparatus 120 and displays the obtained images; however, the exemplary embodiments are not limited to this example. For instance, another arrangement is acceptable in which the terminal apparatus 140 obtains images from the medical image diagnosis apparatus 110 and displays the obtained images.

As explained above, according to the exemplary embodiments, the system, the apparatus, and the method for image processing and the medical image diagnosis apparatus according to an aspect make it possible to easily view the images even when the plurality of images corresponding to the mutually-different time phases are superimposed together.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An image processing system comprising:
   processing circuitry configured to extract a mutually-same region of interest from each of a plurality of pieces of three-dimensional image data corresponding to mutually-different time phases;

determine, on a basis of feature points included in the pieces of three-dimensional image data, a position used for superimposing together the regions of interest extracted from the pieces of three-dimensional image data, in a substantially same position of a subject;

generate a plurality of parallax image groups that the pictures to be viewed change in accordance with shifting of the viewpoints of the viewer, by performing a rendering process on each of the pieces of three-dimensional image data while moving a point-of-view position by a predetermined parallactic angle, so as to include the regions of interest;

hide a part of a region of interest to be on the outside so that a region of interest to be on the inside is exposed, when each of the regions of interest in the plurality of parallax image groups is superimposed; and display, on a display, a superimposed stereoscopic image formed by superimposing the plurality of parallax image groups, so as to superimpose the regions of interest together in the position determined.

2. The image processing system according to claim 1, wherein the processing circuitry is configured to change opacity of each of the regions of interest extracted from the pieces of three-dimensional image data.

3. The image processing system according to claim 1, wherein the processing circuitry is configured to use a gravity point of each of the regions of interest extracted from the pieces of three-dimensional image data, as the feature points.

4. An image processing apparatus comprising:

processing circuitry configured to extract a mutually-same region of interest from each of a plurality of pieces of three-dimensional image data corresponding to mutually-different time phases;

determine, on a basis of feature points included in the pieces of three-dimensional image data, a position used for superimposing together the regions of interest extracted from the pieces of three-dimensional image data, in a substantially same position of a subject;

generate a plurality of parallax image groups that the pictures to be viewed change in accordance with shifting of the viewpoints of the viewer, by performing a rendering process on each of the pieces of three-dimensional image data while moving a point-of-view position by a predetermined parallactic angle, so as to include the regions of interest;

hide a part of a region of interest to be on the outside so that a region of interest to be on the inside is exposed, when each of the regions of interest in the plurality of parallax image groups is superimposed; and display, on a display, a superimposed stereoscopic image formed by superimposing the plurality of parallax image groups, so as to superimpose the regions of interest together in the position determined.

5. An image processing method comprising:

extracting a mutually-same region of interest from each of a plurality of pieces of three-dimensional image data corresponding to mutually-different time phases;

determining, on a basis of feature points included in the pieces of three-dimensional image data, a position used for superimposing together the regions of interest extracted from the pieces of three-dimensional image data, in a substantially same position of a subject;

generating a plurality of parallax image groups that the pictures to be viewed change in accordance with shifting of the viewpoints of the viewer, by performing a rendering process on each of the pieces of three-dimensional image data while moving a point-of-view position by a predetermined parallactic angle, so as to include the regions of interest;

hiding a part of a region of interest to be on the outside so that a region of interest to be on the inside is exposed, when each of the regions of interest in the plurality of parallax image groups is superimposed; and displaying, on a display, a superimposed stereoscopic image formed by superimposing the plurality of parallax image groups, so as to superimpose the regions of interest together in the determined position.

6. A medical image diagnosis apparatus comprising:

processing circuitry configured to extract a mutually-same region of interest from each of a plurality of pieces of three-dimensional image data corresponding to mutually-different time phases;

determine, on a basis of feature points included in the pieces of three-dimensional image data, a position used for superimposing together the regions of interest extracted from the pieces of three-dimensional image data, in a substantially same position of a subject;

generate a plurality of parallax image groups that the pictures to be viewed change in accordance with shifting of the viewpoints of the viewer, by performing a rendering process on each of the pieces of three-dimensional image data while moving a point-of-view position by a predetermined parallactic angle, so as to include the regions of interest;

hide a part of a region of interest to be on the outside so that a region of interest to be on the inside is exposed, when each of the regions of interest in the plurality of parallax image groups is superimposed; and display, on a display, a superimposed stereoscopic image formed by superimposing the plurality of parallax image groups, so as to superimpose the regions of interest together in the position determined.

* * * * *